(12) United States Patent
Sellers

(10) Patent No.: US 8,178,110 B2
(45) Date of Patent: May 15, 2012

(54) REOVIRUS COMPOSITIONS AND METHODS OF USE

(75) Inventor: Holly S. Sellers, Bishop, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 291 days.

(21) Appl. No.: 12/440,762

(22) PCT Filed: Oct. 25, 2007

(86) PCT No.: PCT/US2007/082556
§ 371 (c)(1),
(2), (4) Date: Jun. 12, 2009

(87) PCT Pub. No.: WO2008/076518
PCT Pub. Date: Jun. 26, 2008

(65) Prior Publication Data
US 2010/0055131 A1    Mar. 4, 2010

Related U.S. Application Data

(60) Provisional application No. 60/862,958, filed on Oct. 25, 2006.

(51) Int. Cl.
*A61K 39/15* (2006.01)
(52) U.S. Cl. .................................. 424/215.1; 435/91.33
(58) Field of Classification Search .................. None
See application file for complete search history.

(56) References Cited

U.S. PATENT DOCUMENTS

| | | | |
|---|---|---|---|
| 6,406,702 B1 | 6/2002 | Sharma | |
| 6,951,650 B1 | 10/2005 | van Loon | |
| 2008/0317776 A1 | 12/2008 | Vertommen | |

FOREIGN PATENT DOCUMENTS
EP    1024189 B1    4/2005

OTHER PUBLICATIONS

Goodwin et al, Avian Diseases, 1993, vol. 37, pp. 451-458.*
Heggen-Peay, Avian Disease, 2002, vol. 46, pp. 32-47.*
Sellers et al, Vaccine, 2010, vol. 28, pp. 1253-1263.*
International Search Report and Written Opinion mailed May 23, 2008, issued in corresponding International Application No. PCT/US2007/082556, filed Oct. 25, 2007, 7 pages.
International Preliminary Report on Patentability mailed May 7, 2009, issued in corresponding International Application No. PCT/US2007/082556, filed Oct. 25, 2007, 5 pages.

* cited by examiner

*Primary Examiner* — Ali R. Salimi
(74) *Attorney, Agent, or Firm* — Christensen O'Connor Johnson Kindness PLLC

(57) ABSTRACT

The present invention relates to novel strains of avian reovirus that were isolated from severe cases of Runting Stunting Syndrome in young broiler chickens in southeast United States. The invention is directed to avian reoviruses that impair digestion in poultry, diagnostic assays using nucleotide- or amino acid-specific components of such viruses, and to vaccines that protect chickens from disease caused by such viruses. Nucleotide sequences for the S1 gene, encoding the sigma C minor outer capsid protein, were amplified, and the nucleotide and predicted amino acid sequences were compared with sequences from other recently isolated reovirus field isolates and vaccine strains. Antigenic and molecular characterization of the newly isolated reoviruses revealed a lack of homogeneity with current U.S. isolates, with less than 60% percent amino acid similarity across the sigma C protein. Sequence comparisons with previously reported malabsorption isolates from Europe and Asia revealed a higher amino acid similarity, approaching 80%.

5 Claims, 7 Drawing Sheets

```
Majority    M A G L T P S Q R R E V V G L I L S L T S S V T I S P G D L
            ------------------+------------------+------------------+-
                    10                 20                 30
            ------------------+------------------+------------------+-
42563-4     . . . . . . L . . . . . . . . . . . . . . . . T S . . . . .   30
42563-1     . . . . . . . . . . . . . . . . . . . . . . . . N T N C . . .   30
40963       . . . . . . . . . . . . . . . . . . . . . . N T S . G . . . .   30
40973       . E . . . Q . . . . . . . . . . . . . . . . . . . N . . . .   30
41560       . . . . . . . . . . . . . . . . . . . . . . . A N T N C . . .   30
41565       . . . . . . . . . . . . . . . . . . . . . . N T S . . . . . .   30
55957       . E . N Q . . . . . . . . . . . . . . . . . . A N . . T . . .   30
55958       . E . . . Q . . . . . . . . . . . . . . . . . A N . . T . . .   30
55959       . . . . . L . . . . . . . . . . . . . . . . . A N T N S . . .   30
58554       . . . . . . . . . . . . . . . . M . . . . . . T S . . . . . .   30
58555       . E . . . Q . . . . . . . . . . . . . . . . . . . T . . . . .   30
60403       . . . . . . . . . . . . . . . . . . . . . . . A N T N C . . .   30
54647       . D . . . . . . . . . . . . . . . . . . . . . . N T N C . . .   30
55255       . E . . S Q L . . . . . . . . . . . . . . . . N . . . . . . .   30
55259       . E . . . Q . . . . . . . . . . . . . . . . . N . . . N . . .   30
2408        . . . . N . . . . . . . . . S . . . . . . . . N . . . H . . .   30
S1133       . . . . N . . . . . . . . . S . . . . . . . . N . N . . H . . .   30
1733        . . . . N . . . . . . . . . S . . . . . . . . N . . . H . . .   30

Majority    T P I Y D R L S A L E S A T A S L N E S V S G L L T Q V S D
            ------------------+------------------+------------------+-
                    40                 50                 60
            ------------------+------------------+------------------+-
42563-4     . . . . . . . . V . T I C D T . S G . . G Q . T . M M . N   60
42563-1     . . V . . . . L S . . . V . . . . N . . N . . . Q K . . .   60
40963       . . . . . . . . V . T . C . T . S D . . G Q . A S T T . A   60
40973       . E L R E . V . . . D . . N . . . T . T K . V . D . L V .   60
41560       . . V . . . . L S . . . T I T . . . G . . . D . S R K . . .   60
41565       . . . . . . . . V . T . Y S T . S D . . G Q . A S T T . A   60
55957       . Q L R E . I . . . . . . N . . . . A I E . V . . . L V .   60
55958       A Q . R S . . . . . . . . S N . . . S . T . N . A V S . L V V   60
55959       . . . . . . L S M . . . V . . . S A . . . . . . Q K . . .   60
58554       A . . . . . . . V . T I C . T . S D . . . Q . I S K T . . .   60
58555       . E L R E . V . . . . . . . . . . T I K . V . G . L V .   60
60403       . . V . . . . L S . . . . V . . . . G . . . . X S Q K . L .   60
54647       . . V . . . . L S . . . . V . . . . N . N D . . Q K . . .   60
55255       . E L R E . V . . . . . . . . . . . T . K . V . G . L V .   60
55259       M E L R E . V . . . . . V . . . . G T I K . V . D . L V .   60
2408        . . . . . E . . T I . . A S . E L . H R . I . D I S . T . . N   60
1133        . . . . . E . . T N . . A S . E L . H R . I . D I S . S . . N   60
1733        . . . . . E . . T N . . A S . E L . H R . I . D I S . T . . N   60
```

Figure 1A

```
Majority   L S S K L Q D A A S A L G D L R G D L T S L S T S V Q A L Q
         ------------------+--------------------+--------------------+-
                  70                  80                  90
         ------------------+--------------------+--------------------+-
42563-4  . . A R . D . L T I V S R . M A T . . R N V Q G . . . S . . R   90
42563-1  F E . D . . . V T . S . . Q A N S M . . E . . K E L R Q . S     90
40963    . . T R . D N L V . V S Q . M A N . . R D V Q S R . S . . .     90
40973    . V Q . . G N . . G . I V . . . . E . N . . T . R . . T I .     90
41560    . E . D . . . V I . S . . Q A N S T . . E . . K E L R Q . S     90
41565    . . T R . D . L V . M S Q . I V N . . R D I Q S R . S . F .     90
55957    . . Q . . S N . . D . M V E . . . E . N . . T A . . . I I .     90
55958    . . . R I D N L . A T V A . G Q L E . R . . V M D . K N I R     90
55959    . D . D . . N V T . S . . Q A D S A . . A . . K E L H Q . S     90
58554    . . N R . N G L V N V S Q . I A N . . R D I Q S R . S . . .     90
58555    . A Q . . S N . . D . I V G . . . E . N . . A A . . . T I .     90
60403    . E . G . . . V . . S . . Q T N S T . . E . . K G L R Q . S     90
54647    F E . D . . . . T . S . . Q A N L M . . K . . E D L R Q . S     90
55255    . A Q . . S N . . D . V V E . . . . . N . . T V . . . T I .     90
55259    . A Q . . G N . . G . V V . . . . E . N . . T A . . . T V .     90
2408     I . A N . . . M T H I . D . V T A N . D G . R . T . T . . .     90
S1133    I . A N . . . M T H T . D . V T A N . D G . R . T . T . . .     90
1733     I . A N . . . M T H I . D . V T A N . D G . R . T . T . . .     90

Majority  S S V D S L S T S V S D L S T S V S A H A S S I S N L Q S S
         ------------------+--------------------+--------------------+-
                 100                 110                 120
         ------------------+--------------------+--------------------+-
42563-4  T . L . H . . G D . . . A . . Q . L . . . D . Q L . T . S V .   120
42563-1  . . . . N . V . . . . . . . . . A . . G . Q N A . A D I . A .   120
40963    T . I . . M . S D I . T . . Q . L . N . D . Q . . T . S . .     120
40973    . . L G . . T D . I . . . . G Q . T T N T . . L T . . . G . M   120
41560    G . . . T . V . . . . . . . . . T . . G . Q N A . A A I . T .   120
41565    I . I . . . . S D I . T . . Q . L . N . D . Q . . T . S . .     120
55957    . . L K . . T D . M . . . . D R T T . N T . . . T . . A . K     120
55958    . L L . D V . . T . V S . . A . . R E . D . . . I D . R R Q     120
55959    . . I E N V . . . . . . . V . . T . . G . Q A A . A A V . T .   120
58554    T L . . G V . S D . . L . . Q . L . . . D . Q L . E . S . .     120
58555    . . L R . . T D . . . . . . G Q . T T N . . . . T . V K G M     120
60403    . . . . . . V X . . . . . . . . A . . G . Q D A . V T I . T .   120
54647    . . . . N . V . . . . . . . . . T . . G . Q D A . A A I . T .   120
55255    . . L G . . T E . M . . . . G Q . T T N . . . . T . . R . V     120
55259    . . L E . . T D . M . . . . G Q . T T N T . . L T . . E . T     120
2408     D . . S I . . . N . T . . T N T S . . . . A T L . S . . T T     120
S1133    D . . S I . P . N . T . . T N R S . . . . A I L . S . . T T     120
1733     D . . S I . . . N . T . . T N T S . . . . A T L . S . . T T     120
```

Figure 1B (continued)

```
Majority   V D G L S T D I S N L K R D V S S Q G L N I T D L E Q R V A
         --------------------+--------------------+--------------------+-
                            130                  140                  150
         --------------------+--------------------+--------------------+-
42563-4    . S A . . . . V . . . . . . . . A . S A . . . S . I Q R . . .   150
42563-1    . H A N A . . . N . . . S S . . T I S . . . . . . . . . . . .   150
40963      . S T V A . N V . . . Q . . . A A S A . . . S . . Q R . . .     150
40973      M A . . T V . V T . . . . . . . N . . . Q . . S I . . . . T     150
41560      . H A N T . . . . . . . S S I . T I . . . . . . . . . . . . G   150
41565      . G T . . . . M . . . Q . . . T A S A . . . S . . Q R . . .     150
55957      . . . . T V . V T . . . . . . . N . . . K V . S . . . . . S     150
55958      F G L . . . . T A . . . A . . A A . S . I V . S . . . . . T     150
55959      . H A N T . . . . . . . S S . . T I S . . L A . . . R . . D     150
58554      . S T . . . . M . . . Q . . . T A S A . . . S . . Q . . . .     150
58555      L . . . T V . V A . . . . . A . N . . . K . . . . . . . . .     150
60403      . H A N . . . . . . . R S S . . T I S . . . . . . . . . . E     150
54647      . H A N T . . . . . . . S N . . T I . . . . . . . A . . . .     150
55255      . . . . T V . V A . . . . . M . N . . . K V . G . . . . . .     150
55259      . A . . T V . V T . . . . . . . . . . . Q . . S . . . . . T     150
2408       . . . N . . A . . . . . S . . . . N . . A . . . Q D . . K       150
S1133      . . . N . . A . . . . . S . I . . N . . A . . . Q D . . K       150
1733       . . . N . . A . . . . . S . . . . N . . A . . . Q D . . K       150

Majority   S L E S G S G S S L T F A A P L S L D S G V V S L D M D P Y
         --------------------+--------------------+--------------------+-
                            160                  170                  180
         --------------------+--------------------+--------------------+-
42563-4    A . . . . . . A V . . . R . . . R . . G D S . . . . . . . .     180
42563-1    N I . . . . D . N . R . V S . . N . S Q . . . . I . . . .       180
40963      A . . . S P . . . . . . L . . . R A . G . S . . . . . . . .     180
40973      . . . . . A . . I P . . . . . . K . . . . I . . . . L . . .     180
41560      N I . . . . . P T . K . M S . . . . S Q . . A . . I . . . .     180
41565      A . . . S . . . P . . . L . . . R A . G . S . . . . . . . .     180
55957      . . . . . V . . V P . . . . . . K . E . . T . . . . L . . .     180
55958      A . . . S T . . L P S . S . . . K . . D . T . . . . L . . .     180
55959      D I G . . . . . N . R . S S . . . . S Q . . . . I . . . . .     180
58554      G . . . S . . . . . . . L . . . R V . G . S . . . . . . . .     180
58555      G . . . . . . I P . . . . . . . K . . . . I . . . . L . . .     180
60403      K I . . A S . . . R . T S . . . . S Q . . . . I . . . . . .     180
54647      N I . . S . . . R . V S . . . . S Q . . . . I . . . . . . .     180
55255      D . . . . A . . L P . . . . . . K . . . . . . . . . L . . .     180
55259      . . . . . A . . I P . . . . . . K . . . I . . . . L . . .       180
2408       . . . . T A S H G . S . S P . . . V A D . . . . . . . . . .     180
S1133      . . . . T A S H G . S L S P . . . V A D . . . . . . . . . .     180
1733       . . . . T A S H G . S . S P . . . V A D . . . . . . . . . .     180
```

Figure 1C (continued)

```
Majority    F C S V R H N L T S Y S A S A Q L M Q F Q W L V R G E G G S
            ------------------+--------------------+--------------------+-
                    190                 200                 210
            ------------------+--------------------+--------------------+-

42563-4     . . . E . A . . . . . . . . . . . . L . . . . F . . S . D . .    210
42563-1     . . . D N K A . . . . . T D . . . . . . . . . A . . . D . .      210
40963       . . . E . A . . . . . . . . . . . . L . . . . F . . S . . . .    210
40973       . . . . N . . . . . . . . . . L . . N . . . . . . . . . . .      210
41560       . . . D N K A . . . . . T D . . . . . . . . . A . . . D . .      210
41565       . . . E . A . . . . . . . . . . . . L . . . . F . . S . . . .    210
55957       . . . . D . . . . . . . . . . I . . N . . . . . . S . . . .      210
55958       . . . . D . . . . . . . . . . . . . . . . . . F . . . . . .      210
55959       . . . D N Q A . . . . . T D . . . . . . . . . A . . . . . .      210
58554       . . . E . S . . . . . . . . . . . . L . . . . Y . . S . . . .    210
58555       . . . . D . . . . . . . . S . . N . . . . . . . . . . . . .      210
60403       . . . D N M A . . . . . T D . . . . . . . . . A . . . D . .      210
54647       . . . D N K A . . . . . T D . . . . . . . . . A . . . D . .      210
55255       . . . . D . . . . . . . . S . . N . . . . . . . . . . . . .      210
55259       . . . . D . . . . . . . . . . L . . N . . . . . . . . . . .      210
2408        . . . Q . V S . . . . . . E . . . . . . R . M A . . T N . .      210
S1133       . . . Q . V S . . . . . E . E . . . . . . R . M E . . T N . .    210
1733        . . . Q . V S . . . . . . E . . . . . . R . M A . . T N . .      210

Majority    S D S I D M L V N A H C H G R R T D Y M M S T T Q S L T V T
            ------------------+--------------------+--------------------+-
                    220                 230                 240
            ------------------+--------------------+--------------------+-

```
Majority      G N S V S L V F D L D Y I T S P P S D Y S R L I P C H G F Q
         --------------------+--------------------+--------------------+-
                            250                  260                  270
         --------------------+--------------------+--------------------+-
42563-4   . . . . . . . . N . . . . . . . G V . . A . . . . . . . . .    270
42563-1   . . . . . . . . N . . . . . K . . . . M . . . V . R A . . .    270
40963     . . . . . . . . N . . . . . T S G V . . A . . . . . . . . .    270
40973     . . . . T . . . . . N A L I . . . . . . . . . . . . . . . .    270
41560     . . . . . . . . S . . . . . K . . . . I . . . V . R V . . .    270
41565     . . . . . . . . N . . H . . T S G V . . A . . . . . . . . .    270
55957     . . P . T . . . . . N A L I . . . . . . . . . . . . . . . .    270
55958     . T . . . . . . . . N T L V T . . . . . . . . . . . . . . .    270
55959     D . . . . . . . N . . . . . K . . . . M . . . . . R A . . .    270
58554     . . . . . . . . N . . . . . T S G V E . A . . . . S . . . .    270
58555     . . . . T . . . . . N A L I . . . . . . . . . . . . . . . .    270
60403     . . . . . . . . N . . . . . K . . . . M . . . V . R A . . R    270
54647     . . . . . . . . N . . . . . K . . . . M . . . V . R A . . .    270
55255     . . . . T . . . . . N A L I . . . . . . . . . . . . . . . .    270
55259     . . . . T . . . . . N A L I . . . P . . . . . . . . . . . .    270
2408      S . V . L . T . . . S D . . H I . . . L A . . V . S A . . .    270
S1133     S . V . L . T . . . S D . . H I . . . L A . . V . S A . . .    270
1733      S . V . L . T . . . S D . . H I . . . L A . . V . S A . . .    270

Majority      Q A T F P V D V S F T R D D T T H A Y Q V Y G A F S S P R V
         --------------------+--------------------+--------------------+-
                            280                  290                  300
         --------------------+--------------------+--------------------+-
42563-4   . . . . . . . I . . . K S . V . . T . . . . . . . D G . . .    300
42563-1   A . S . . . . . . . . . T . P . . . . . . . . . . . . . . I    300
40963     . . . . . . . I . . . K N . . . . T . . . . . . . N G . . .    300
40973     . . . . . . . L . . K . . . V M . S . . . . . S Y T T . . I    300
41560     A . S . . . . . . . . . . . A . P . . . . . . . . . . . . .    300
41565     . . . . . . . I . . . K N . . . . T . . . . . . . D G . . .    300
55957     . . . . . . . L . . K . . . V . . S . . . . . S Y T T . . .    300
55958     . . . . . . . L . . K . . E E . . S . . . . . S Y . T . A C    300
55959     A . S . . . . . . . . . . . T . . . . . . . . T . . . . . I    300
58554     . . . . . . . I . . . N . . . . . T . . . . . . . D G . . .    300
58555     . . . . . . . L . . K . . . V . . S . . . . . S Y T T . . .    300
60403     A . S . . . . . . . . . T . P . . . . . . . . . . . . . . I    300
54647     A . S . . . . . . . . . T . P . . . . . . . . . . . . . . I    300
55255     . . . . . . . L . . K . . . V I . S . . . . . S Y T T . . .    300
55259     . . . . . . . L . . K . . . V . . S . . . . . S Y T T . . I    300
2408      A . S . . . . . . . . . S A . . . . . . A . . V Y . . S . .    300
S1133     A . S . . . . . . . . . S A . . . . . . A . . V Y . . S . .    300
1733      A . S . . . . . . . . . S A . . . . . . A . . V Y . . S . .    300
```

Figure 1E (continued)

```
Majority   F K I T F S P - G G T G T A N I R F L T V R T G I D T
        ------------------+-------------------+----------------
                         310                 320
        ------------------+-------------------+----------------
42563-4  . . V . . . . - . E . . A T . . . . . . . . . . . .     327
42563-1  . . . . . L T - . . . . . . L . . . . . . . . . . .     326
40963    . . V . . . . - . . . S . T . . . . . . . . . . . .     327
40973    . . . . . . . - . N P V P . V . . . I . . . . . . .     326
41560    . . . . . L T - . . . . . . L . . . . . . . . . . .     326
41565    . . V . . . . - . . . S . T S V . . . . . . . . . .     326
55957    . . . . . . . - . N P V P . V . . . I . . . . . . .     326
55958    L . V . . . W . F Q L P . V . . . . . L .                322
55959    . . . . . L T - . . . . C K H S . . E P A .              322
58554    . . V . . . . - . E N Q H D Q M C D S .                  319
58555    . . . . . . . - . N P V P . V . . . I . G D              321
60403    . . . . . L T - . . . . . . L . . . . . . . . . . .     326
54647    . . . . . L T - . . . . . . L . .                        317
55255    . R . . . . . - . N P V P . V . . . I . G D E            322
55259    . . . . . . . - . N . S A C G H T . I S                  319
2408     . T . . . P T - . . D . . . . . S . . . . . . T . .     327
S1133    . T . . . P T - . . D . . . . . S . . . . . . . . .     326
1733     . T . . . P T - . . D . . . . . S . . . . . . . . .     326
```

Figure 1F (continued)

REOVIRUS COMPOSITIONS AND METHODS OF USE

CROSS-REFERENCE TO RELATED APPLICATIONS

This application claims the benefit of U.S. Provisional Application Ser. No. 60/862,958, filed Oct. 25, 2006.

FIELD OF THE INVENTION

The present invention relates to novel strains of avian reovirus that were isolated from severe cases of Runting Stunting Syndrome in young broiler chickens in the southeast United States. The invention is directed to avian reoviruses that impair digestion in poultry, diagnostic assays using nucleotide- or amino acid-specific components of such viruses, such as the S1 gene encoding the sigma C minor outer capsid protein, and to vaccines that protect chickens from disease caused by such viruses.

BACKGROUND OF THE INVENTION

Avian and mammalian reoviruses comprise the genus *Orthoreovirus* in the family Reoviridae. These viruses contain 10 dsRNA genome segments enclosed within a non-enveloped, icosahedral double capsid of approximately 80 nm (Joklik, W. K. In: The reoviridae. W. K. Joklik, ed. Plenum Press, New York, pp. 9-78, 1983; Schnitzer, T. J. et al. J. Virol. 43: 1006-1014, 1982). The genome segments can be separated based on electrophoretic mobility into three large (L1, 2,3), three medium (M1,2,3) and four small (S1,2,3,4) segments which encode proteins $\lambda 1, \lambda 2, \lambda 3, \mu 1, \mu 2, \mu NS, \sigma 3, \sigma 1, \sigma 2, \sigma NS$, respectively (Spandidos D. A., and Graham, A. F., J. Virol. 19: 968-976, 1976; Varela, R. and Benavente, J., J. Virol. 68: 6775-6777, 1994; Wu, W. Y. et al., J. Virol. Methods 48: 119-122, 1994). The $\sigma 2$ protein is an outer capsid protein which carries group-specific neutralizing epitopes, binds double-stranded RNA, and has been identified as a zinc metalloprotein (Wickramsinghe et al., Virology 194:688-696, 1993; Nibert, M. L. and Schiff, L. A., In: Fields virology, $4^{th}$ ed., vol. 2. Knipe, D. M., and Howley, P. M., eds. Lippincott Williams & Wilkins, Philadelphia, Pa., p. 3087, 2001).

Avian reoviruses (ARV) are a diverse group of poultry pathogens whose virulence varies greatly, among isolates within different hosts. ARVs have been isolated from turkeys with poult enteritis and mortality syndrome (PEMS) (Heggen-Peay, C. L., et al., Avian Dis. 46: 32-47, 2002) as well as from chickens and ducks. These isolates have been associated with enteric and respiratory disease (Fahey, J. E., and Crawley, J. F., Can. J. Comp. Med. 18: 13-21, 1954), viral arthritis/tenosynovitis (Glass, S. E., et al., Avian Dis. 17: 415-424, 1973), malabsorption and stunting syndrome (Rosenberger, J. K., In: Diseases of poultry, $11^{th}$ ed. Barnes, H. J., et al., eds. Iowa State University Press, Ames Iowa, pp. 284-293, 2003). Not all reoviruses are highly virulent, as they can be isolated from chickens or turkeys exhibiting no clinical signs of disease.

RSS is a disease of domesticated chickens that causes a variety of symptoms, such as delayed growth, lack of flock uniformity, a small liver with an enlarged gall bladder, pale, thin, almost translucent, intestinal walls, large amounts of fluid inside the small and large intestines, occasional increased amount of pericardial fluid, and sporadic white, or cream-colored, plaques in individual proventricular glands. Various microscopic lesions have also been observed, and frequently noted as multiple cysts in the intestinal crypts. The early lesion is clinically considered to be a form of cystic enteropathy, and which evolves into an inflammatory lesion causing cystic enteritis. As the lesions progress, they may result in shortening and clubbing of the intestinal villi. Outbreaks of RSS reduce the growth rate, body weight, and size, and increase the mortality in affected chicken populations.

Runting-Stunting Syndrome can been reproduced in the clinic. Gavage inoculations with intestinal contents from affected chickens, for example, cause RSS in the inoculated chickens. Inoculation with filtered gut contents from affected chickens can also cause RSS, suggesting that a virus is responsibly for the syndrome, since the filters used to inoculate the gut contents are able to exclude bacteria. RSS has also been reproduced in experiments that place healthy broiler chickens on litter contaminated by affected chickens.

Runting-Stunting Syndrome has a significant economic impact on the chicken farming industry. Delayed growth during the first few weeks of age, for example, increases the cost of feed conversion. In 2004, broiler companies across the southeast United States began seeing more cases of Runting-Stunting Syndrome (RSS) during the winter and spring seasons. Losses due to RSS at one company were estimated to be over $100,000 per week per million birds. These impacts demonstrate a continuing need for compositions and methods for ameliorating at one or more symptoms of RSS, for identifying and characterizing the causative agent(s) of RSS, and for preventing the onset of RSS in chickens.

While viral agents, environmental conditions, and genetic factors are all believed to play a role in determining the susceptibility of chickens to RSS, vaccines against various infectious agents hold much promise in containing this and related diseases. Vaccines can be divided into two general groups: live (attenuated) vaccines, and inactivated vaccines. Live vaccines can present of all the relevant immunogenic determinants of an infectious agent in their natural forms to the host's immune system, and because they can multiply in the vaccinated host, only require a small amount of the immunizing agent. Safety is often a concern with live vaccines, however, as they may induce disease in immuno-compromised animals, or they may revert to a virulent form, leading to more serious infections. Live vaccines may also impair reproductive function. Inactivated vaccines by comparison are generally far safer than live vaccines. One major disadvantage, however, is their intrinsically low immunogenicity (i.e., ability to trigger the host's immune system). Adjuvants with significant immunostimulatory capabilities are often necessary, then, to augment the immunogenicity of inactivated immunogens to reach a minimum potential suitable for preventing disease in a vaccinated bird or preventing the spread of infection and disease to unvaccinated birds.

Vaccination of poultry is useful for several reasons. One purpose is to prevent egg production losses in commercial layers. Vaccines may also be used to reduce the level of transmission by eggs in breeding stock or as a tool for eradicating disease in infected flocks on multi-age production sites. Thus there remains a need for safe, efficacious, and inexpensive vaccines that sufficient to protect poultry susceptible to etiological agents, such as avian reoviruses, that may cause Runting Shunting Syndrome or related diseases. Vaccines effective against avian reoviruses, for example, may optionally be combined with vaccines that protect poultry from other commercially-troublesome infectious diseases. The formulation should also be stable, and provide lasting protection without undesirable side effects.

SUMMARY OF THE INVENTION

The present invention relates to a composition comprising an isolated avian reovirus comprising an S1 protein comprising the amino acid sequence set forth in the group consisting of SEQ ID NOS: 2, 4, 6, 8, 10, 12, 14, 16, 18, 20, 22, 24, 26, 28, and 30.

The invention also relates to a vaccine comprising antigenic material derived from an avian reovirus wherein said reovirus comprises an S1 protein comprising an amino acid sequence set forth in the group consisting of SEQ ID NOS: SEQ ID NOS: 2, 4, 6, 8, 10, 12, 14, 16, 18, 20, 22, 24, 26, 28, and 30, wherein said antigenic material is selected from the group consisting of live virus, live attenuated virus, inactivated virus, and one or more immunologically active subcomponents, thereof.

The invention also relates to a method of eliciting an immune response in a chicken, the method comprising the step of introducing into a chicken a composition comprising an isolated reovirus comprising an S1 protein comprising the amino acid sequence set forth in the group consisting of SEQ ID NOS: 2, 4, 6, 8, 10, 12, 14, 16, 18, 20, 22, 24, 26, 28, and 30.

The invention also relates to a method for measuring the amount of a reovirus in a chicken, the method comprising the steps of: (a) contacting a chicken sample with an antibody that selectively binds to a reovirus that comprises an S1 protein that comprises an amino acid sequence selected from the group set forth in SEQ ID NOS: 2, 4, 6, 8, 10, 12, 14, 16, 18, 20, 22, 24, 26, 28, and 30, and (b) measuring the amount of binding of the antibody to a component of the chicken sample.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 1A-1F sets forth a sequence alignment among avian reoviruses based on their sigma C(S1) amino acid sequences. The alignment was performed using ClustalW software.

DEFINITIONS

Figure 2:
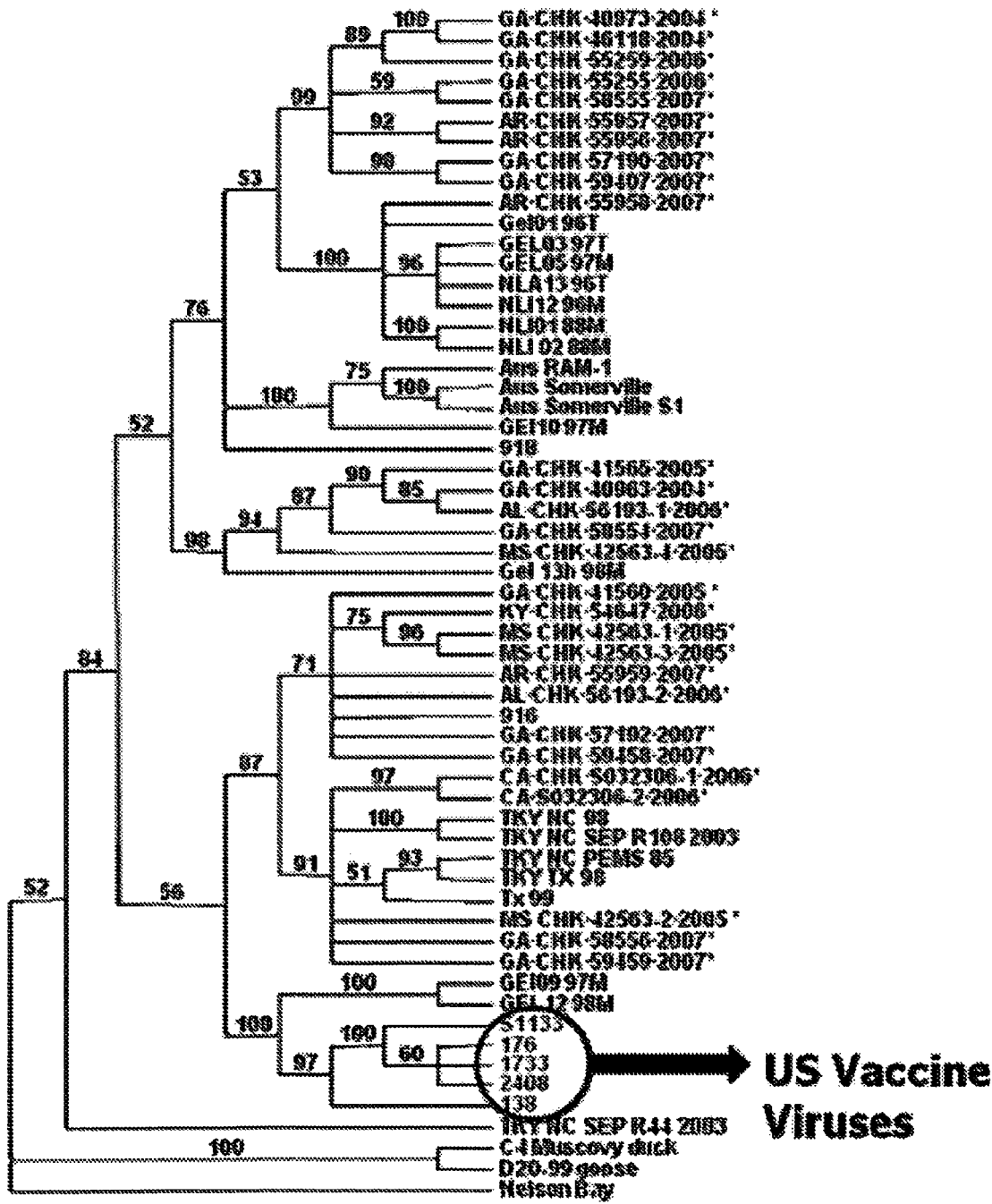
FIG. 2 sets forth the phylogenetic relationships among avian reoviruses based on the sigma C(S1) amino acid sequences. The phylogenetic tree was constructed following amino acid alignment by neighbor-joining method using maximum parsimony analysis. The nomenclature for naming of the reoviruses is typically State/Species/Case ID/Year of Isolation. Reoviruses isolated by the inventors from clinical cases of Runting and Stunting Syndrome are indicated with an asterisk. U.S. vaccine viruses are circled.

The following is a list of terms and their definitions used throughout the specification and the claims:

The term "isolated" when used with respect to a reovirus, means a reovirus that is substantially free from the cellular components that are associated with the reovirus as it is found in nature. In this context, "substantially free from cellular components" means that the reovirus is purified to a level of greater than 80% (such as greater than 90%, greater than 95%, or greater than 99%).

The term "isolated reovirus" means reoviruses that have been isolated from cellular components and then combined with pharmaceutically-acceptable components (e.g., carriers, adjuvants, and/or diluents) to facilitate the administration of the reovirus to a chicken for the subsequent production of antibodies against the reovirus.

The term "Galliformes" refers to an order of birds containing turkeys, grouse, chickens, quails, and pheasants. About 256 species are found worldwide.

Abbreviations and their corresponding meanings include: aa or AA=amino acid; ARV=avian reovirus; MAS=malabsorption syndrome mg=milligram(s); ml or mL=milliliter(s); mm=millimeter(s); mM=millimolar; nmol=nanomole(s); pmol=picomole(s); ppm=parts per million; RSS=Runting Stunting Syndrome; RT=room temperature; U=units; ug, μg=microgram(s); ul, μl=microliter(s); uM, μM=micromolar.

DETAILED DESCRIPTION OF THE PREFERRED EMBODIMENT

The present invention relates to compositions and vaccines comprising antigenic components capable of protecting birds of the order Galliformes, including chickens, against Runting Stunting Syndrome. The compositions and vaccines may comprise an avian reovirus, or one or more of its subcomponents, capable of stimulating a protective immune response. The invention also relates to methods of stimulating an immune response by administering said compositions or vaccines to a susceptible bird.

The invention relates to a composition comprising an isolated avian reovirus comprising an S1 protein comprising the amino acid sequence set forth in SEQ ID NOS: 2, 4, 6, 8, 10, 12, 14, 16, 18, 20, 22, 24, 26, 28, and 30.

The composition may comprise the isolated reovirus designated as strain 40973, or a progeny thereof. Reovirus strain 40973 has been deposited in the American Type Culture Collection, 10001 University Boulevard, Manassas, Va., on Oct. 20, 2005, and accorded has ATCC accession number PTA-7174. Compositions of the invention may further comprising a pharmaceutically acceptable carrier, adjuvant, or diluent. The compositions may comprise an isolated live reovirus, a live reovirus that is attenuated, or an isolated reovirus that is inactivated. The invention also relates to compositions comprising at least $10^2$ titration units of the reovirus. The invention also relates to compositions that further comprise additional isolated virus particles that are different from the isolated reovirus comprising an S1 protein comprising the amino acid sequence set forth in the group consisting of SEQ ID NOS: 2, 4, 6, 8, 10, 12, 14, 16, 18, 20, 22, 24, 26, 28, and 30. Examples of additional isolated virus particles include infectious bronchitis virus, Newcastle disease virus, infectious bursal disease virus, fowl adenovirus, EDS virus, and turkey rhinotracheitis virus.

The invention also relates to a method of eliciting an immune response in a chicken, the method comprising the step of introducing into a chicken a composition comprising an isolated reovirus comprising an S1 protein comprising the amino acid sequence set forth in the group consisting of SEQ ID NOS: 2, 4, 6, 8, 10, 12, 14, 16, 18, 20, 22, 24, 26, 28, and 30. One aspect of the invention relates to a method wherein the isolated reovirus is reovirus strain 40973, ATCC accession number PTA-7174. Another aspect of the invention relates to a method wherein the composition further comprises a pharmaceutically acceptable carrier, adjuvant, or diluent. The composition may comprise an attenuated live reovirus or an inactivated reovirus. Another aspect of the invention relates to a method wherein the composition comprises at least $10^2$ titration units of the reovirus. The compositions of the invention may be introduced into the chicken on multiple occasions, such as during a time period extending from day 1 after hatching to week 18 after hatching. The invention also relates to method of eliciting an immune response in a chicken, using compositions comprising an isolated reovirus, as described above, wherein the composition further comprises additional isolated virus particles selected from the group consisting of infectious bronchitis virus, Newcastle disease virus, infectious bursal disease virus, fowl adenovirus, EDS virus, and turkey rhinotracheitis virus.

The invention also relates to a vaccine comprising antigenic material derived from an avian reovirus wherein said reovirus comprises an S1 protein comprising an amino acid sequence selected from the group consisting of SEQ ID NOS: 2, 4, 6, 8, 10, 12, 14, 16, 18, 20, 22, 24, 26, 28, and 30, wherein said antigenic material is selected from the group consisting of live virus, live attenuated virus, inactivated virus, and one or more immunologically active subcomponents, thereof. One aspect of the invention relates to a vaccine wherein said reovirus comprises an S1 protein comprising the amino acid sequence set forth in SEQ ID NO: 2.

Another aspect of the invention relates to a combination vaccine, comprising antigenic material derived from an avian reovirus and one or more vaccines selected from the group consisting of infectious bronchitis virus vaccine, Newcastle disease virus vaccine, infectious bursal disease virus vaccine, fowl adenovirus vaccine, EDS virus vaccine, and turkey rhinotracheitis virus vaccine.

The invention also relates to a method for measuring the amount of a reovirus in a chicken, the method comprising the steps of: (a) contacting a chicken sample with an antibody that selectively binds to a reovirus that comprises an S1 protein that comprises an amino acid sequence set forth in the group consisting of SEQ ID NOS: 2, 4, 6, 8, 10, 12, 14, 16, 18, 20, 22, 24, 26, and 30, and (b) measuring the amount of binding of the antibody to a component of the chicken sample. One aspect of the invention relates to a method of the invention wherein an ELISA is used to measure the amount of binding of the antibody to a component of the chicken sample.

The present invention also relates to an isolated reovirus strain, exemplified by the strain designated 40973 and related viruses, which can be identified by the amino acid sequence of their small segment 1 (S1, sigma C, or σC) outer capsid protein, set forth in the group consisting of SEQ ID NOS: 2, 4, 6, 8, 10, 12, 14, 16, 18, 20, 22, 24, 26, 28, and 30. Strain 40973 and these related viruses, for example, causes at least some of the symptoms of Runting-Stunting Syndrome, when the virus is administered to healthy chickens.

The present invention provides compositions that comprise an isolated reovirus comprising an S1 protein comprising the amino acid sequence set forth in SEQ ID NO: 2. The invention also provides a novel isolated reovirus designated strain 40973. The invention also provides methods of eliciting an immune response in a chicken against a reovirus.

One aspect of the invention relates to compositions that each comprise an isolated reovirus, wherein the isolated reovirus comprises an S1 protein that comprises an amino acid sequence set forth in the group consisting of SEQ ID NOS: SEQ ID NOS: 2, 4, 6, 8, 10, 12, 14, 16, 18, 20, 22, 24, 26, 28, and 30. The composition can be, for example, a liquid, gel or solid (e.g., powder). The compositions of this aspect of the invention can be used, for example, to store strain 40973 or related viruses for future use or characterization (e.g., as a dry powder); to characterize strain 40973 or related viruses (e.g., in a liquid composition to assess the specificity of antibodies directed against strain 40973); to propagate strain 40973 or related viruses (e.g., as inoculum used to inoculate growth media to grow more virus particles).

Compositions of the invention can also be used to raise antibodies against strain 40973, or related viruses, such as those described in Table 1. For example, in some embodiments, compositions of the present invention comprise strain 40973 particles, or particles from related viruses, and at least one pharmaceutically acceptable carrier (e.g., saline) and, optionally, an adjuvant or diluent. These compositions can be administered to a chicken in order to raise antibodies in the chicken against strain 40973 or related viruses.

Some compositions of the present invention are vaccines that cause the production of antibodies against strain 40973 or related viruses in vaccinated chickens. The antibodies protect the chickens from disease caused by subsequent infection by reovirus strain 40973 or related viruses.

Compositions of the invention can also, for example, be attached to a solid substrate and used to purify anti-40973 antibodies, or antibodies from related viruses, which releasably bind to the immobilized composition.

The present invention provides compositions that each comprise an isolated reovirus, wherein the isolated reovirus comprises an S1 protein that comprises an amino acid sequence set forth in SEQ ID NOS: 2, 4, 6, 8, 10, 12, 14, 16, 18, 20, 22, 24, 26, 28, and 30. The isolated reovirus can be in a live, live attenuated, or inactivated form.

An example of an isolated reovirus that comprises an S1 protein that comprises the amino acid sequence set forth in SEQ ID NO: 2 is avian reovirus strain 40973. SEQ ID NO: 2 shows the amino acid sequence of the S1 protein from the avian reovirus strain designated 40973.

An isolated reovirus that comprises an S1 protein that comprises an amino acid sequence set forth in SEQ ID NOS: 2, 4, 6, 8, 10, 12, 14, 16, 18, 20, 22, 24, 26, 28, and 30 can be isolated from an infected chicken. A typical broiler to be used for this purpose shows the following signs: the secretion of too liquid faeces and/or maldigested feed resulting in growth retardation.

By way of example, the intestine is isolated from the affected chicken followed by homogenization of the organ in a suitable buffer. Thereafter, the homogenized tissue is clarified by centrifugation and the supernatant is filtrated through filters with a pore size of 0.2 µm. A sample of the filtrate is added to freshly prepared primary chicken cells, preferably chicken embryo liver (CEL) cells, prepared from specific pathogen free (SPF) embryos, and observed daily for the presence of a cytopathic effect (CPE). If no CPE is present after 5 to 6 days, a freeze/thawed suspension of the first monolayer is added to freshly prepared CEL cells. If after the first passage or the second passage CPE is observed, then the virus is further characterized by its in vivo properties in broilers to induce decreased body weight and lack of uniformity, and by determining the amino acid sequence of its S1 protein. A more detailed method for the isolation of an avian reovirus that comprises an S1 protein that comprises the amino acid sequence set forth in SEQ ID NO: 2 is disclosed in Example 1.

An avian reovirus that comprises an S1 protein that comprises an amino acid sequence set forth in SEQ ID NOS: 2, 4, 6, 8, 10, 12, 14, 16, 18, 20, 22, 24, 26, 28, and 30 can be isolated from other parts of an infected chicken, such as the liver of affected broiler chickens or from the faeces excreted by such a broiler chicken.

Compositions of the present invention that are formulated to be administered to a chicken (e.g., vaccines) may comprise physiologically-acceptable carrier. Examples of physiologically-acceptable carriers include, but are not limited to, sterile water, aqueous saline solutions (e.g., a 0.9% NaCl solution), phosphate buffers, aqueous dextrose or glycerol solutions, proteins, and sugars.

Compositions of the present invention that are formulated to be administered to a chicken to elicit an immune response in the chicken can optionally comprise an adjuvant. Examples of adjuvants include, but are not limited, to aluminum hydroxide, aluminum phosphate, aluminum oxide, oil-in-water or water-in-oil emulsion based on, for example a mineral oil, such as Bayol F° or Marcol 52® or a vegetable oil such as vitamin E acetate, and saponins.

Compositions of the present invention include, for example, compositions that elicit an immune response in a chicken. The immune response may, or may not, confer protective immunity on the chicken. An immune response may, for example, include one or more of the following: (a) a cell mediated immune response, which involves the production of lymphocytes in response to exposure to the antigen; and/or (b) a humoral immune response, which involves production of plasma lymphocytes (B cells) in response to antigen exposure with subsequent antibody production.

Compositions of the present invention include, for example, vaccines. The term "vaccine", as used herein, broadly refers to any composition that may be administered to a chicken to cause the production of antibodies that protect the animal against disease caused by a reovirus that comprises an S1 protein that comprises an amino acid sequence set forth in the group consisting of SEQ ID NOS: 2, 4, 6, 8, 10, 12, 14, 16, 18, 20, 22, 24, 26, 28, and 30. A vaccine of the present invention comprises an isolated reovirus (that comprises an S1 protein that comprises an amino acid sequence set forth in the group consisting of SEQ ID NOS: 2, 4, 6, 8, 10, 12, 14, 16, 18, 20, 22, 24, 26, 28, and 30), a physiologically acceptable carrier, and optionally, an adjuvant and/or diluent.

The isolated reovirus can be incorporated into the vaccine as a live attenuated or inactivated virus. The ability of the avian reovirus to induce some, or all, of the symptoms of Runting-Stunting Syndrome is significantly reduced, or completely absent, if the avian reovirus is in a live attenuated or inactivated form.

Attenuation of an avian reovirus useful in the practice of the present invention can be achieved by methods well known in the art for this purpose, such as disclosed in Gouvea et al. (*Virology* 126:240-247, 1983). Briefly, and by way of example, after the isolation of the virus from a target animal, a viral suspension is inoculated onto primary chicken embryo liver cells. If the isolate is not able to produce cytopathic effects (CPE), then the virus is passaged repeatedly (e.g., 3-10 times) until CPE is observed. As soon as CPE is visible, cells and cell culture fluids are collected, frozen and thawed, clarified by centrifugation and the supernatant containing the avian reovirus isolate is aliquoted and stored at −20° C. This process may be repeated (e.g., 10-100 times) to further attenuate the virus.

A vaccine according to the invention can be prepared by conventional methods such as, for example, commonly used for the commercially available live and inactivated reovirus vaccines. The preparation of veterinary vaccine compositions is described, for example, in *Vaccines for Veterinary Applications* (Peters, A. R., et al., eds., Butterworth-Heinemann Ltd, 1993). In brief, a susceptible substrate is inoculated with an avian reovirus according to the invention in a live or live attenuated form, and propagated until the virus is replicated to a desired infectious titer, or antigen mass content. Reovirus containing material is then harvested and formulated to a pharmaceutical composition with prophylactic activity.

Any substrate which is able to support the replication of an isolated avian reovirus of the present invention, if necessary after adaptation of the avian reovirus to the substrate, can be used to produce a vaccine according to the present invention. Suitable substrates include primary (avian) cell cultures, such as chicken embryo liver cells (CEL), chicken embryo fibroblasts (CEF) or chicken kidney cells (CK), mammalian cell lines such as the VERO cell line or the BGM-70 cell line, or avian cell lines such as QT-35, QM-7 or LMH. Usually, after inoculation of the cells, the virus is propagated for 3-10 days, after which the cell culture supernatant is harvested and, if desired, filtered or centrifuged in order to remove cell debris. Alternatively, an isolated avian reovirus according to the invention can be propagated in embrocated chicken eggs followed by harvesting the avian reovirus material by routine methods.

Vaccines of the present invention comprising a live attenuated virus can be prepared and marketed in the form of a (frozen) suspension or in a lyophilized form. The vaccine additionally contains a pharmaceutically acceptable carrier or diluent customarily used for such compositions. Carriers include stabilizers, preservatives and buffers. Suitable stabilizers are, for example, carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate, and gentamicin. Diluents include water, aqueous buffer (such as buffered saline), alcohols, and polyols (such as glycerol).

Although administration by injection (e.g., intramuscular, subcutaneous) of the live vaccine is possible, the live vaccine is preferably administered by the inexpensive mass application techniques commonly used for avian reovirus vaccination. These techniques include introducing the vaccine into drinking water imbibed by chickens, and spray vaccination. Alternative methods for the administration of the live vaccine include in ovo, eye drop, and beak dipping administration.

Vaccines of the present invention can also comprise an inactive form of an isolated reovirus that comprises an S1 protein that comprises an amino acid sequence set forth in the group consisting of SEQ ID NOS: 2, 4, 6, 8, 10, 12, 14, 16, 18, 20, 22, 24, 26, 28, and 30. An advantage of an inactivated vaccine is the elevated levels of protective antibodies of long duration that can be obtained. This property makes such an inactivated vaccine particularly suited for breeder vaccination.

The aim of inactivation of the viruses after the propagation step is to prevent the viruses from replicating. In general, this can be achieved by chemical or physical means. Chemical inactivation can be effected by treating the viruses with, for example, enzymes, formaldehyde, β-propiolactone, ethylene-imine or a derivative thereof. If necessary, the inactivating compound is neutralized afterwards. Material inactivated with formaldehyde can, for example, be neutralized with thiosulphate. Physical inactivation can preferably be carried out by subjecting the viruses to energetic radiation, such as UV light or γ-rays. If desired, after treatment, the pH can be adjusted to a value of about 7.

A vaccine comprising the inactivated avian reovirus can, for example, comprise one or more of the above-mentioned pharmaceutically acceptable carriers or diluents suited for this purpose.

Typically, an inactivated vaccine according to the invention comprises one or more compounds with adjuvant activity. Suitable compounds or compositions for this purpose include aluminum hydroxide, -phosphate or -oxide, oil-in-water or water-in-oil emulsion based on, for example a mineral oil, such as Bayol F° or Marcol 52® or a vegetable oil such as vitamin E acetate, and saponins. Inactivated vaccines are usually administered parenterally (e.g., intramuscularly or subcutaneously).

A vaccine according to the invention has an effective dosage of the avian reovirus as the active component, i.e., an amount of immunizing avian reovirus material that will induce immunity in the vaccinated birds or their progeny against challenge by a virulent reovirus that comprises an S1 protein that comprises an amino acid sequence set forth in SEQ ID NOS: 2, 4, 6, 8, 10, 12, 14, 16, 18, 20, 22, 24, 26, 28, and 30. Immunity is defined herein as the induction of a significant higher level of protection in a population of birds after vaccination compared to an unvaccinated group.

Typically, the live vaccine according to the invention can be administered in a dose of not less than $10^2$ titration units (wherein titration units are defined in Title 9, Section 113.332, Code of Federal Regulations) per bird, and an inactivated vaccine may contain the antigenic equivalent of $10^4$-$10^{10}$ $TCID_{50}$ per bird (wherein TCID is an abbreviation for Tissue Culture Infective Dose).

The avian reovirus vaccine according to the present invention may be used effectively in chickens. Chickens include broilers, reproduction stock, and laying stock. Chickens can be vaccinated at any suitable age, and are usually about one to three days old before first vaccination. The chickens may be vaccinated only once. Optionally, when two doses of vaccine are used, the first is given, for example, when the chickens are 3 days to a week old and subsequently after a further 1-10 weeks.

Multiple doses of the composition can be administered throughout the life of the chicken. As maternal immunity is a primary source of providing protection to broiler progeny, breeder chickens are typically vaccinated, although broiler chickens can be vaccinated if so desired.

The following, exemplary, vaccination regime can be applied to breeders, grandparents, and to great-grandparents:
Day 1: Mild live tissue culture attenuated (subcutaneous).
Weeks 3-4: Attenuated live (oral in the drinking water).
Weeks 6-7: Attenuated live (oral in the drinking water).
Week 12: Killed vaccine (subcutaneous or intramuscular).
Week 18: Killed vaccine (subcutaneous or intramuscular).

Broilers may, for example, be vaccinated directly at one day of age with the live attenuated vaccine according to the invention. Vaccination of parent stock, such as broilers breeders, can be done with a live mild attenuated or inactivated vaccine according to the invention, or with combinations of both. The advantages of this type of immunization program includes the immediate protection of one-day-old progeny provided by maternally derived antibodies vertically transmitted to the young birds. A further example of a breeder vaccination program includes the vaccination of the breeders at one day of age with a live vaccine, and again at 6 weeks of age with a live attenuated vaccine, followed by a vaccination between 14-18 weeks of age with an inactivated vaccine. Alternatively, the live vaccination may be followed by two vaccinations with inactivated vaccines on 10-12 weeks and 16-18 weeks of age.

The invention also includes combination vaccines including, in addition to an isolated reovirus that comprises an S1 protein that comprises the amino acid sequence set forth in SEQ ID NO: 2, one or more vaccine components of other pathogens infectious to poultry. Typically, the vaccine components in the combination vaccine are the live attenuated or inactivated forms of the pathogens infectious to poultry. For example, a combination vaccine of the present invention can comprise one or more (inactivated) vaccine strains of reovirus, infectious bronchitis virus (IBV), Newcastle disease virus (NDV), infectious bursal disease virus (IBDV), fowl adenovirus (FAV), EDS virus and turkey rhinotracheitis virus (TRTV).

In another aspect, the present invention provides methods of eliciting an immune response in a chicken (*Gallus gallus*). The methods of this aspect of the invention each comprise the step of introducing into a chicken a composition that comprises an isolated reovirus that comprises an S1 protein that comprises an amino acid sequence set forth in SEQ ID NOS: 2, 4, 6, 8, 10, 12, 14, 16, 18, 20, 22, 24, 26, 28, and 30. By way of example, the isolated reovirus can be reovirus strain 40973. The compositions typically comprises a pharmaceutically acceptable carrier, and may optionally comprise an adjuvant and/or diluent. The elicited immune response may, or may not, provide the chicken with immunity to further infection by an isolated reovirus that comprises an S1 protein that comprises an amino acid sequence set forth in the group consisting of SEQ ID NOS: 2, 4, 6, 8, 10, 12, 14, 16, 18, 20, 22, 24, 26, 28, and 30. The compositions of the present invention (that comprise an isolated reovirus, wherein the isolated reovirus comprises an S1 protein that comprises an amino acid sequence set forth in the group consisting of SEQ ID NOS: 2, 4, 6, 8, 10, 12, 14, 16, 18, 20, 22, 24, 26, 28, and 30) can be used in the practice of the methods of the present invention.

The composition (that comprises an isolated reovirus that comprises an S1 protein that comprises an amino acid sequence set forth in the group consisting of SEQ ID NOS: 2, 4, 6, 8, 10, 12, 14, 16, 18, 20, 22, 24, 26, 28, and 30) can be introduced into the chicken by any useful route; for example by intramuscular, intradermal or subcutaneous injection (e.g., by injection into the muscles of the breast, wing, leg, tail, head, or neck), or via intranasal or oral administration (e.g., administration on feed or in drinking water, gels, or sprays). The composition can be administered to a chicken, for example, by a syringe or a needleless apparatus (e.g., Pigjet or Biojector (Bioject, Oregon, USA)).

In another aspect, the present invention provides methods for measuring the amount of a reovirus in a chicken, wherein the reovirus comprises an S1 protein that comprises an amino acid sequence set forth in the group consisting of SEQ ID NOS: 2, 4, 6, 8, 10, 12, 14, 16, 18, 20, 22, 24, 26, 28, and 30. The methods of this aspect of the invention comprise the steps of (a) contacting a chicken sample with an antibody that selectively binds to a reovirus that comprises an S1 protein that comprises an amino acid sequence set forth in the group consisting of SEQ ID NOS: 2, 4, 6, 8, 10, 12, 14, 16, 18, 20, 22, 24, 26, 28, and 30, and (b) measuring the amount of binding of the antibody to a component of the chicken sample. The antibody can, for example, selectively bind to a portion of the S1 protein that comprises an amino acid sequence set forth in SEQ ID NOS: 2, 4, 6, 8, 10, 12, 14, 16, 18, 20, 22, 24, 26, 28, and 30. The chicken sample can be any biological material obtained from a chicken, such as tissue, bone, blood, urine or faeces. The methods of this aspect of the invention are useful, for example, for determining whether chickens are infected with a reovirus that comprises an S1 protein that comprises an amino acid sequence set forth in SEQ ID NOS: 2, 4, 6, 8, 10, 12, 14, 16, 18, 20, 22, 24, 26, 28, and 30. Infected chickens can be killed in order to prevent spread of the reovirus to other chickens.

By way of example, the amount of a reovirus in a chicken can be measured using an Enzyme Linked Immunoassay (abbreviated as ELISA). In the practice of a sandwich-style ELISA, the standards and unknowns are incubated in microtiter wells pre-coated with antibody that captures the reovirus. The samples and standards are diluted in a buffer containing detergent for 1 hour at room temperature prior to loading the microtiter wells. The captured reovirus particles are then detected with tracer-linker antibody (e.g., biotinylated second antibody) that binds to the reovirus which is then detected, for example by using a streptavidin-peroxidase conjugate and colored substrate (e.g., TMB). If TMB is used as the colored substrate then color development is measured at a wavelength of 450 nanometers. The concentration of the reovirus particles in experimental samples is determined using a standard curve prepared from known amounts of the reovirus particles. ELISA techniques are well known to those of ordinary skill in the art and are described, for example, in *ELISA and Other Solid Phase Immunoassays: Theoretical and Practical Aspects*, Kemeny, D. M., and S. J. Challacombe, eds., Wiley, 1989.

Antibodies useful in the practice of the present invention include monoclonal antibodies, polyclonal antibodies, single chain antibodies, humanized antibodies, or fragment thereof, also including bispecific antibody, synthetic antibody, antibody fragment, such as Fab, Fv or scFv fragments etc., or a chemically modified derivative of any of these. Monoclonal antibodies can be prepared, for example, by the techniques as originally described in Köhler and Milstein (*Nature* 256:495, 1975), and Galfré, (*Meth. Enzymol.* 73:3, 1981), which, in brief, involves the fusion of mouse myeloma cells to spleen cells derived from immunized mammals. Furthermore, antibodies, or fragments thereof, can be obtained by using methods which are described, for example, in Harlow and Lane, *Antibodies, A Laboratory Manual*, CSH Press, Cold Spring Harbor, 1988. When derivatives of said antibodies are obtained by the phage display technique, surface plasmon resonance as employed in the BIAcore system can be used to increase the binding efficiency of the phage antibodies (Schier, *Human Antibodies Hybridomas* 7:97-105, 1996; Malmborg, *J. Immunol. Methods* 183:7-13, 1995). The production of chimeric antibodies is described, for example, in WO89/09622. Methods for the production of humanized antibodies are described in, for example, EP-A1 0 239 400 and WO90/07861. A further source of antibodies that can be utilized in accordance with the present invention are so-called xenogenic antibodies. The general principle for the production of xenogenic antibodies, such as human antibodies in mice, is described in, for example, WO 91/10741, WO 94/02602, WO 96/34096 and WO 96/33735. Useful antibodies can exist in a variety of forms besides complete antibodies; including, for example, Fv, Fab and F(ab)2, as well as in single chains (see e.g., WO88/09344).

Useful antibodies, or their corresponding immunoglobulin chain(s), can be further modified using conventional techniques known in the art, for example by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art (see, e.g., Sambrook, *Molecular Cloning: A Laboratory Manual*, Cold Spring Harbor Laboratory (1989) N.Y.).

EXAMPLES

The foregoing discussion may be better understood in connection with the following representative examples which are presented for purposes of illustrating the principle methods and compositions of the invention and not by way of limitation. Various other examples will be apparent to the person skilled in the art after reading the present disclosure without departing from the spirit and scope of the invention. It is intended that all such other examples be included within the scope of the appended claims.

General Materials and Methods

All parts are by weight (e.g., % w/w), and temperatures are in degrees centigrade (° C.), unless otherwise indicated.

Example 1

This Example describes the isolation of avian reovirus strain 40973 and related viruses.

Viruses

Reovirus field isolates, chicken/GA 40973/2005, chicken/AL 40963/2005, chicken/GA 41560/2005, and chicken/GA 41565/2005 were isolated at the Poultry Diagnostic and Research Center at the University of Georgia, from the intestines or feces of chickens exhibiting enteritis. Field isolate chicken/GA 46118/2005 was isolated from a proventricular plaque from an experimentally infected bird. Table 1 provides a summary of the viruses characterized or referred to in all of the studies cited in the Examples. All viruses were isolated and propagated in primary chicken embryo liver cells prepared from 9-11 day of embryonation specific pathogen free (SPF) embryos. All isolates were passaged a total of four times. Upon the development of 70-80% cytopathic effect, observed as syncytial formation, the cell cultures were frozen and stored at −80° C. Each cell culture was frozen and thawed three times before each virus passage in cultured cells.

TABLE 1

Table of Viruses

| Species | State of isolation | Identification # | Year of isolation | Tissue submitted |
|---|---|---|---|---|
| Chicken | GA | 40973 | 2005 | Intestines |
| Chicken | AL | 40963 | 2005 | Proventriculus |
| Chicken | GA | 41560 | 2005 | Intestines |
| Chicken | GA | 41565 | 2005 | Intestines |
| Chicken | GA | 46118 | 2005 | Proventriculus |
| Chicken | AR | 55957 | 2006 | Intestines |
| Chicken | AR | 55958 | 2006 | Intestines |
| Chicken | AR | 55959 | 2006 | Intestines |
| Chicken | GA | 58554 | 2007 | Intestines |
| Chicken | GA | 58555 | 2007 | Intestines |
| Chicken | GA | 60403 | 2007 | Intestines |
| Chicken | KY | 54647 | 2006 | Tendon, spleen |
| Chicken | GA | 55255 | 2006 | Spleen |
| Chicken | GA | 55259 | 2006 | Spleen |
| Chicken | MS | 42563-1 | 2005 | Intestines |
| Chicken | MS | 42563-4 | 2005 | Intestines |

Table 2 identifies the nucleotide and amino acid or protein sequences used in the Examples or referred to in this application.

TABLE 2

Table of Sequences

| Name (Isolate) | SEQ ID NO S1 gene (nt) | SEQ ID NO Sigma C (aa) | Description (nt, aa) |
|---|---|---|---|
| 40973 | 1 | 2 | GenBank DQ872797, GenBank ABJ09658.1 |
| 40963 | 3 | 4 | GenBank DQ872796, GenBank ABJ09657.1 |
| 41560 | 5 | 6 | GenBank DQ872798, GenBank ABJ09659.1 |
| 41565 | 7 | 8 | GenBank DQ872799, GenBank ABJ09660.1 |
| 42563-1 | 9 | 10 | GenBank DQ872800, GenBank ABJ09661.1 |
| 42563-4 | 11 | 12 | GenBank DQ872801, GenBank ABJ09662.1 |
| 55957 | 13 | 14 | |
| 55958 | 15 | 16 | |
| 55959 | 17 | 18 | |
| 58554 | 19 | 20 | |
| 58555 | 21 | 22 | |
| 60403 | 23 | 24 | |
| 54647 | 25 | 26 | |
| 55255 | 27 | 28 | |
| 55259 | 29 | 30 | |
| Primer P1 | | 31 | 5'-agt att tgt gag tac gat tg-3' |
| Primer P4 | | 32 | 5'-agt att tgt gag tac gat tg-3' |

RNA Extraction

Total viral RNA was extracted from primary chicken embryo liver cell passages using the RNeasy kit (Qiagen, Valencia, Calif.) according to the manufacturer's recommendations. Briefly, 48 hours post infection, cell culture media was decanted and the monolayer was lysed with lysing buffer.

RT-PCR

A cDNA corresponding to the S1 gene was produced by reverse transcription and PCR using SuperScript™ III RNase H⁻ reverse transcriptase and Platinum®Taq DNA polymerase (Invitrogen, Carlsbad, Calif.) using the following primers (Kant, A., et al., *Vet. Res.* 34:203-212, 2003):

```
                                        (SEQ ID NO: 31)
P1 (5'- agt att tgt gag tac gat tg -3')
and
                                        (SEQ ID NO: 32)
P4 (5'- ggc gcc aca cct tag gt -3').
```

The 1.1 kb amplified products were separated on a 1.0% agarose gel, stained with ethidium bromide and visualized with an ultraviolet transilluminator. The fragment was excised, purified with the QIAEX II gel extraction kit (Qiagen Inc., Valencia, Calif.), and eluted in diethylpyrocarbonate (DEPC)-treated water.

Cloning of Reovirus S1 Gene

The gel-extracted DNA from the amplification reaction was cloned into plasmid pCR 2.1 (Invitrogen) according to the manufacturer's instructions. Several clones containing plasmids with the 1.1 kb insert were identified by PCR. The clones were expanded and the plasmid DNA purified using Qiagen plasmid miniprep kit according to methods provided by the manufacturer.

Direct Nucleotide Sequencing of Amplified Products

Purified plasmids and gel-purified PCR products were sequenced with universal sequencing primers or Reovirus S1-specific oligonucleotide primers, respectively, using double-stranded DNA sequencing methods using fluorescently-labeled dideoxynucleotides and Taq polymerase on an ABI 9700 automated sequencer (Applied Biosystems Inc., Foster City, Calif.). A 2× or greater sequence coverage of the S1 gene was obtained for each isolate, with regions of ambiguity resolved by re-sequencing across the desired region.

Sequence Analysis

Nucleotide sequence editing, predicted amino acid sequence analysis, and multiple alignments of the S1 gene and sigma C protein were performed using CLUSTAL V (Lasergene, v. 5.0, DNASTAR, Madison, Wis.).

Example 2

This example describes the in vivo evaluation of reovirus isolate 40973, and shows that strain 40973 adversely affects the growth of chickens.

Virus Isolation

A reovirus field isolate was isolated in primary chicken embryo liver cells (CeLic) from the intestines of 13-day-old commercial broilers experiencing a severe clinical presentation of Runting Stunting Syndrome. Briefly, intestines were homogenized in virus transport medium containing antibiotics, and filtered through a 0.45 micron sterile filter. Complete monolayers of primary CeLic were inoculated with 0.2 ml of the intestinal homogenate. Cell cultures were examined daily. The cell cultures were frozen and stored at −80° C. when 70-80% cytopathic effect, noted as syncytial formation, was obtained. Cell cultures were frozen and thawed three times before subsequent cell culture passages or titration.

Virus Titration

Titration of virus strain 40973 was performed in primary CeLic in a 96 well microtiter format. Briefly, virus was diluted 1:10 in the first row of the microtiter plate and serially diluted out to the $10^{th}$ well. A virus and cell control were also included in the plate. Primary cells were added to each well and incubated at 37° C. with 5% $CO_2$. At 96 hours post-inoculation, the cell culture media was decanted, and the cells fixed with methanol and stained with crystal violet. The titer was obtained from the reciprocal of the last dilution where 50% cytopathic effect was observed in the well. The final titer of virus strain 40973 was $10^5$ tissue culture infective dose $(TCID)_{50}$/ml.

Chickens

Forty, one-day-old, non-vaccinated commercial broilers were obtained from a local hatchery. Four treatment groups of 10 birds each were placed in forced air positive-pressure Horsfal-Bauer isolation units. Birds were given food and water ad libitum. One group, designated as the negative control birds, was sham-challenged with 0.1 ml sterile phosphate buffered saline (PBS) via the footpad (FP). A second group of negative control birds was sham-challenged with 0.1 ml sterile PBS via the intratracheal (IT) route. A third treatment group was challenged via the FP with $10^3$ $TCID_{50}$/ml. The fourth treatment group was challenged via IT with $10^3$ $TCID_{50}$/ml. At two weeks of age, the body weight and length of each bird was recorded and they were humanely sacrificed.

Statistics

Statistical analysis of the data by the Holm-Sidak method of one way analysis of variance (ANOVA) was performed using SigmaStat software.

TABLE 3

Average Body Weights and Lengths From Each Treatment Group

| Treatment group | Mean Body Weights (grams) | Std. Dev. | Mean Body Lengths (cm) | Std. Dev |
|---|---|---|---|---|
| Negative control Sham IT Challenge | 146.92[a] | 10.1 | 28.85[a] | 1.07 |
| Negative control Sham FP Challenge | 151.45[a] | 9.17 | 28.78[a] | 1.18 |
| 40973 IT Challenge | 132.1[b] | 11.5 | 27.13[b] | 0.68 |
| 40973 FP Challenge | 116.51[b] | 9.12 | 26.37[c] | 0.96 |

Groups with different letters ([a], [b], or [c]) were significantly different at $p \leq 0.001$.

Example 3

Virus Isolation

Reovirus field isolates, chicken/GA 40973/2005, chicken/GA 41560/2005, chicken/GA 41565/2005, were isolated at the Poultry Diagnostic and Research Center at the University of Georgia, from the intestines or feces of chickens exhibiting RSS/enteritis. Field isolate chicken/GA 46118/2005 and chicken/AL 40963/2005, were isolated from the proventriculi of RSS-affected experimental birds. Organs (proventriculi or intestines) from clinically-affected chickens were individually homogenized in virus transport media with antibiotics. The homogenized tissues were filtered through a 0.45 micron syringe filter. The filtrates were incubated with Reovirus S1133 antisera (Charles River, SPAFAS, Wilmington, Mass.) at 37° C. for 1 hour. Following neutralization, 0.2 ml of homogenate was inoculated in primary chicken embryo liver cells and cultured for a total of four passages. Upon the development of 70-80% cytopathic effect, observed as syncytial formation, the cell cultures were frozen and stored at −80° C. Cell cultures were frozen and thawed three times prior to subsequent cell culture passage. Viruses designated chicken/MS 42563-1/2005, chicken/MS 42563-2/2005, chicken/MS 42563-3/2005, and chicken/MS 42563-4/2005 were isolated from broilers and submitted to the laboratory for molecular characterization.

RNA Extraction

Total viral RNA was extracted from primary chicken embryo liver cell passages using the RNeasy kit (Qiagen, Valencia, Calif.) according to the manufacturer's recommendations. Briefly, 48 hours post infection, cell culture media was decanted, the monolayer overlaid with 300 µl RLT buffer containing 0.143 M β-mercaptoethanol and scraped with a cell scraper as recommended by the manufacturer.

RT-PCR

A cDNA corresponding to the S1 gene was produced by reverse transcription and PCR using SuperScript™ III RNase H⁻ reverse transcriptase and Platinum®Taq DNA polymerase (Invitrogen, Carlsbad, Calif.) with previously published P1 and P4 primers, SEQ ID NOS: 31 and 32, respectively (Kant, A., et al., *Vet. Res.* 34:203-212, 2003). The 1.1 kb amplified products were separated on a 1.0% agarose gel, stained with ethidium bromide and visualized with a UV transilluminator. The fragment was excised, purified with the QIAEX II gel extraction kit (Qiagen Inc., Valencia, Calif.), eluted in diethylpyrocarbonate (DEPC)-treated water, and stored at −80° C.

Nucleotide Sequencing of Amplified Products and S1 Clones

Gel-purified PCR products were sequenced directly using double-stranded DNA sequencing with fluorescently-labeled dideoxynucleotides and Taq polymerase and performed on an ABI 9700 automated sequencer (Applied Biosystems Inc., Foster City, Calif.) (16). PCR primers P1 (SEQ ID NO: 31) and P4 (SEQ ID NO: 32), along with conserved internal S1 gene primers located in conserved regions, were used as needed to complete sequencing. The nucleotide sequences of all primers used for sequencing are available upon request. In addition, gel purified products were cloned into plasmid pCR2TOPO (Invitrogen) and transformed into competent *E. coli* cells according to protocols provided by the manufacturer. Several clones from each isolate containing plasmids with the 1.1 kb insert were identified by PCR using commercially-available M13 forward and reverse primers. The clones were expanded and the plasmid-purified using a plasmid mini-prep kit (Qiagen, Valencia, Calif.) according to methods of the manufacturer. M13 universal forward and reverse primers along with internal S1 primers were used as needed to complete sequencing. At least three clones or PCR products from three amplifications containing the S1 gene were sequenced in both directions and used to obtain the consensus sequence.

Sequence Analysis

Nucleotide, predicted amino acid sequence analysis and multiple alignments of the S1 gene and sigma C protein were performed using CLUSTAL W (Lasergene, v. 5.0, DNASTAR, Madison, Wis.). Sequences for the S1 genes of previously published avian reoviruses were obtained from GenBank and had the following accession numbers: DQ872796, chicken/AL 40963/2005; DQ872797, chicken/GA 40973/2005; DQ872798, chicken/GA 41560/2005; and DQ872799, chicken/GA 41565/2005. FIG. 1 illustrates a multiple sequence alignment of avian reovirus sigma C(S1) amino acid sequences of the invention.

Aligned sequences were compared and a phylogram was generated using maximum parsimony analysis with Neighbor-Joining clustering (Gojobori, T. et al., J. Mol. Evol. 18: 414-423, 1982; Saitou, N. et al., Mol. Biol. Evol. 4: 406-425, 1987) and 1000 bootstrap replicates (confidence levels listed in parentheses) in a heuristic search using the Phylogenetic Analysis Using Parsimony v 4.10b software (PAUP) (Swofford, D. Sinauer and Associates, Inc. Sunderland, Mass., 2001). Predicted antigenic regions within sigma C were obtained using the software program designed by Kolaskar (bio.dfci.harvard.edu/tools/antigenic.html; Kolaskar A. S., and Tongaonkar, P C., FEBS letter 176:172-174, 1990). FIG. 2 illustrates the phylogenetic relationships among avian reoviruses based on the sigma C(S1) amino acid sequences determined by sequencing the S1 genes obtained from avian reoviruses of the invention.

GenBank Accession Numbers

Sequences obtained for several chicken isolates described here have been submitted to GenBank and assigned the following accession numbers: DQ872796-DQ872801.

Monoclonal Antibody Profiles

Several reovirus field isolates were sent to Intervet, Inc. (Boxmeer, The Netherlands) for reovirus monoclonal antibody profiling using a plaque reduction assay based on growth in primary chicken embryo liver cell cultures (van Loon, A. A., et al., Vet. Quart. 23(3):129-33, 2001) (Table 4).

TABLE 4

| | Monoclonal antibody reactivity pattern | | | | |
|---|---|---|---|---|---|
| | Monoclonal antibodies[4] | | | | |
| Isolates | 154 | 13-6 | 15-1 | 14-67 | 14-11 |
| S1133* | + | + | + | + | + |
| 2408* | + | + | + | + | + |
| 1733* | + | + | − | + | + |
| CO8* | + | + | + | + | − |
| ERS-1* | + | − | − | + | − |
| ERS-2* | + | − | − | + | − |
| 40963 | + | − | − | + | − |
| 46118 | + | − | − | + | − |
| 41560 | + | − | − | + | − |
| 41565 | + | − | − | + | − |
| 42563-1 | + | − | − | + | − |
| 42563-2 | + | − | − | + | − |

*van Loon, A. A., et al., Vet. Quart. 23(3): 129-33, 2001.

These results demonstrate that many of the recent southeast United States reovirus isolates have the same reactivity pattern as several European reovirus isolates (ERS).

While the preferred embodiments of the invention have been illustrated and described, it will be appreciated that various changes can be made therein without departing from the spirit and scope of the invention. All references, patents, or applications cited herein are incorporated by reference in their entirety, as if written herein.

---

SEQUENCE LISTING

```
<160> NUMBER OF SEQ ID NOS: 32

<210> SEQ ID NO 1
<211> LENGTH: 981
<212> TYPE: DNA
<213> ORGANISM: Avian orthoreovirus
<220> FEATURE:
<221> NAME/KEY: CDS
<222> LOCATION: (1)..(981)

<400> SEQUENCE: 1 atg gaa ggc tta act cag tca cag cga aga gag gtc gtg ggg ctg ata        48
Met Glu Gly Leu Thr Gln Ser Gln Arg Arg Glu Val Val Gly Leu Ile
1               5                   10                  15 ctc tca ttg act tcg agc gtg act ata aat cct ggc gat ttg acg gaa        96
Leu Ser Leu Thr Ser Ser Val Thr Ile Asn Pro Gly Asp Leu Thr Glu
            20                  25                  30 ctg cgt gag cgc gtc tcg gcg tta gac tcg gcc aat gcg tcg ttg acc       144
Leu Arg Glu Arg Val Ser Ala Leu Asp Ser Ala Asn Ala Ser Leu Thr
        35                  40                  45 gaa acc gta aaa ggc gtg tta gat cag ttg gta gat ttg gta cag aag       192
Glu Thr Val Lys Gly Val Leu Asp Gln Leu Val Asp Leu Val Gln Lys
    50                  55                  60 ttg ggc aat gcg gcg ggt gct ata gtt gac cta cga gga gag cta aac       240
Leu Gly Asn Ala Ala Gly Ala Ile Val Asp Leu Arg Gly Glu Leu Asn
65                  70                  75                  80 tca tta act acc aga gtc caa act atc caa tcc tct ttg gga tca ctc       288
Ser Leu Thr Thr Arg Val Gln Thr Ile Gln Ser Ser Leu Gly Ser Leu
                85                  90                  95 acg gac agt ata tcg gat ctt tct ggc caa gtg act act aac acc tct       336
Thr Asp Ser Ile Ser Asp Leu Ser Gly Gln Val Thr Thr Asn Thr Ser
```

```
            100                 105                 110
tcg ctc acg aat ctg ggg agt atg atg gct ggt ctc aca gtc gat gtg    384
Ser Leu Thr Asn Leu Gly Ser Met Met Ala Gly Leu Thr Val Asp Val
        115                 120                 125 act aat ctt aaa cgc gac gta tcg aat cag ggt ctt caa att acg agt    432
Thr Asn Leu Lys Arg Asp Val Ser Asn Gln Gly Leu Gln Ile Thr Ser
130                 135                 140 atc gag cag cgt gta act agt ttg gaa tct ggt gct gga tct att ccc    480
Ile Glu Gln Arg Val Thr Ser Leu Glu Ser Gly Ala Gly Ser Ile Pro
145                 150                 155                 160 aca ttt gct gct ccc ctt aaa tta gat agc ggg att gta tca ctc gac    528
Thr Phe Ala Ala Pro Leu Lys Leu Asp Ser Gly Ile Val Ser Leu Asp
            165                 170                 175 ctg gat cct tac ttt tgt tct gtg aac cat aat ctc acg tcg tat tcc    576
Leu Asp Pro Tyr Phe Cys Ser Val Asn His Asn Leu Thr Ser Tyr Ser
            180                 185                 190 gca agc gct ctg cta atg aat ttt cag tgg ctt gtt cga ggt gag gga    624
Ala Ser Ala Leu Leu Met Asn Phe Gln Trp Leu Val Arg Gly Glu Gly
            195                 200                 205 gga tcg tct gat tca ttc gat atg aat gtg aca gct cat agt cac ggc    672
Gly Ser Ser Asp Ser Phe Asp Met Asn Val Thr Ala His Ser His Gly
    210                 215                 220 cag agg aca gat ttt atg atg tct act act cag tcg tta act gtt act    720
Gln Arg Thr Asp Phe Met Met Ser Thr Thr Gln Ser Leu Thr Val Thr
225                 230                 235                 240 gga aat tct gtc act cta gtc ttt gat ctt aac gcg ctt att tct ccc    768
Gly Asn Ser Val Thr Leu Val Phe Asp Leu Asn Ala Leu Ile Ser Pro
                245                 250                 255 ccc tct gac tat tct cgt ttg ata cca tgt cat ggt ttt caa caa gcg    816
Pro Ser Asp Tyr Ser Arg Leu Ile Pro Cys His Gly Phe Gln Gln Ala
            260                 265                 270 acg ttc cca gtg gac ctt tcg ttt aag cga gac gac gtc atg cat tca    864
Thr Phe Pro Val Asp Leu Ser Phe Lys Arg Asp Asp Val Met His Ser
            275                 280                 285 tat cag gtg tat ggt tct tac aca act ccc cgc att ttc aag ata aca    912
Tyr Gln Val Tyr Gly Ser Tyr Thr Thr Pro Arg Ile Phe Lys Ile Thr
    290                 295                 300 ttc tcc cct ggc aat cca gtg cct gcg gtc ata cgt ttc ata acc gtg    960
Phe Ser Pro Gly Asn Pro Val Pro Ala Val Ile Arg Phe Ile Thr Val
305                 310                 315                 320 cgt acg ggc atc gat act taa                                         981
Arg Thr Gly Ile Asp Thr
            325

<210> SEQ ID NO 2
<211> LENGTH: 326
<212> TYPE: PRT
<213> ORGANISM: Avian orthoreovirus

<400> SEQUENCE: 2

Met Glu Gly Leu Thr Gln Ser Gln Arg Arg Glu Val Val Gly Leu Ile
1               5                   10                  15

Leu Ser Leu Thr Ser Ser Val Thr Ile Asn Pro Gly Asp Leu Thr Glu
            20                  25                  30

Leu Arg Glu Arg Val Ser Ala Leu Asp Ser Ala Asn Ala Ser Leu Thr
        35                  40                  45

Glu Thr Val Lys Gly Val Leu Asp Gln Leu Val Asp Leu Val Gln Lys
    50                  55                  60

Leu Gly Asn Ala Ala Gly Ala Ile Val Asp Leu Arg Gly Glu Leu Asn
65                  70                  75                  80
```

```
Ser Leu Thr Thr Arg Val Gln Thr Ile Gln Ser Ser Leu Gly Ser Leu
                85                  90                  95

Thr Asp Ser Ile Ser Asp Leu Ser Gly Gln Val Thr Thr Asn Thr Ser
            100                 105                 110

Ser Leu Thr Asn Leu Gly Ser Met Met Ala Gly Leu Thr Val Asp Val
        115                 120                 125

Thr Asn Leu Lys Arg Asp Val Ser Asn Gln Gly Leu Gln Ile Thr Ser
    130                 135                 140

Ile Glu Gln Arg Val Thr Ser Leu Glu Ser Gly Ala Gly Ser Ile Pro
145                 150                 155                 160

Thr Phe Ala Ala Pro Leu Lys Leu Asp Ser Gly Ile Val Ser Leu Asp
                165                 170                 175

Leu Asp Pro Tyr Phe Cys Ser Val Asn His Asn Leu Thr Ser Tyr Ser
            180                 185                 190

Ala Ser Ala Leu Leu Met Asn Phe Gln Trp Leu Val Arg Gly Glu Gly
        195                 200                 205

Gly Ser Ser Asp Ser Phe Asp Met Asn Val Thr Ala His Ser His Gly
    210                 215                 220

Gln Arg Thr Asp Phe Met Met Ser Thr Thr Gln Ser Leu Thr Val Thr
225                 230                 235                 240

Gly Asn Ser Val Thr Leu Val Phe Asp Leu Asn Ala Leu Ile Ser Pro
                245                 250                 255

Pro Ser Asp Tyr Ser Arg Leu Ile Pro Cys His Gly Phe Gln Gln Ala
            260                 265                 270

Thr Phe Pro Val Asp Leu Ser Phe Lys Arg Asp Asp Val Met His Ser
        275                 280                 285

Tyr Gln Val Tyr Gly Ser Tyr Thr Thr Pro Arg Ile Phe Lys Ile Thr
    290                 295                 300

Phe Ser Pro Gly Asn Pro Val Pro Ala Val Ile Arg Phe Ile Thr Val
305                 310                 315                 320

Arg Thr Gly Ile Asp Thr
                325

<210> SEQ ID NO 3
<211> LENGTH: 978
<212> TYPE: DNA
<213> ORGANISM: Avian orthoreovirus
<220> FEATURE:
<221> NAME/KEY: CDS
<222> LOCATION: (1)..(978)
<220> FEATURE:
<221> NAME/KEY: misc_feature
<222> LOCATION: (978)..(978)
<223> OTHER INFORMATION: N = a, c, g or t

<400> SEQUENCE: 3 atg gcc gga ctc act cca tca cag cga aga gaa gtc gtc ggg cta ata      48
Met Ala Gly Leu Thr Pro Ser Gln Arg Arg Glu Val Val Gly Leu Ile
1               5                   10                  15 ctc tca ttg act tcg aac acg agt ata ggt cct gga gat ttg aca ccg      96
Leu Ser Leu Thr Ser Asn Thr Ser Ile Gly Pro Gly Asp Leu Thr Pro
            20                  25                  30 atc tac gat cgt ctc tcg gcc gtt gag aca gct tgc gcc act tta agt     144
Ile Tyr Asp Arg Leu Ser Ala Val Glu Thr Ala Cys Ala Thr Leu Ser
        35                  40                  45 gac tct gtg ggc caa tta gct tca acg aca tct gct tta tcc act cgt     192
Asp Ser Val Gly Gln Leu Ala Ser Thr Thr Ser Ala Leu Ser Thr Arg
    50                  55                  60
```

```
ttg gat aac ttg gtg agt gtg tca caa gat atg gct aat gac ctg agg      240
Leu Asp Asn Leu Val Ser Val Ser Gln Asp Met Ala Asn Asp Leu Arg
 65                  70                  75                  80 gat gtt caa agt cgc gtg tct gca ctt caa aca tcg ata gat agt atg      288
Asp Val Gln Ser Arg Val Ser Ala Leu Gln Thr Ser Ile Asp Ser Met
                 85                  90                  95 tcc agt gac att tcc acc tta tca caa tcg ctg tct aat cac gat tcc      336
Ser Ser Asp Ile Ser Thr Leu Ser Gln Ser Leu Ser Asn His Asp Ser
            100                 105                 110 cag att tcc acg ctt tcc tct tct gtc agc act gta gca act aac gtg      384
Gln Ile Ser Thr Leu Ser Ser Ser Val Ser Thr Val Ala Thr Asn Val
        115                 120                 125 tcc aac ctt caa cgt gac gtg gct gca tct gca ctc aac att tct gat      432
Ser Asn Leu Gln Arg Asp Val Ala Ala Ser Ala Leu Asn Ile Ser Asp
    130                 135                 140 ctt cag cga cgt gtt gct gct ctg gaa tcg agt ccc ggt tca tcc ctt      480
Leu Gln Arg Arg Val Ala Ala Leu Glu Ser Ser Pro Gly Ser Ser Leu
145                 150                 155                 160 aca ttt ctt gct ccc ctg cgg gct gat ggt ggc tcc gtc tca tta gat      528
Thr Phe Leu Ala Pro Leu Arg Ala Asp Gly Gly Ser Val Ser Leu Asp
                165                 170                 175 atg gat ccg tat ttt tgc tca gaa agg gcg aac tta acg tcc tac tcg      576
Met Asp Pro Tyr Phe Cys Ser Glu Arg Ala Asn Leu Thr Ser Tyr Ser
            180                 185                 190 gcg agt gcg cag ctg ctg cag ttt cag tgg ttc gtc agg agt gag gga      624
Ala Ser Ala Gln Leu Leu Gln Phe Gln Trp Phe Val Arg Ser Glu Gly
        195                 200                 205 ggt tcc tca gac tcg att aac atg agc gtg gtg gcc cat tgc cac ggt      672
Gly Ser Ser Asp Ser Ile Asn Met Ser Val Val Ala His Cys His Gly
    210                 215                 220 cgt cgt acg gac tat ctg atg tcc tct cat gac tca ctc acc gtc act      720
Arg Arg Thr Asp Tyr Leu Met Ser Ser His Asp Ser Leu Thr Val Thr
225                 230                 235                 240 ggc aac tca gtg tct tta gtg ttc aac ttg gat tac att act acg tct      768
Gly Asn Ser Val Ser Leu Val Phe Asn Leu Asp Tyr Ile Thr Thr Ser
                245                 250                 255 ggt gtg gat tat gct cgt ctg att ccg tgt cat ggt ttt cag caa gcc      816
Gly Val Asp Tyr Ala Arg Leu Ile Pro Cys His Gly Phe Gln Gln Ala
            260                 265                 270 act ttt cct gtt gac atc tct ttc acg aag aat gat act aca cac acg      864
Thr Phe Pro Val Asp Ile Ser Phe Thr Lys Asn Asp Thr Thr His Thr
        275                 280                 285 tac caa gtc tat ggc gca ttt aat ggc cct cgc gtc ttt aag gtg acc      912
Tyr Gln Val Tyr Gly Ala Phe Asn Gly Pro Arg Val Phe Lys Val Thr
    290                 295                 300 ttc tct ccg ggt ggg act agc acg aca aac ata cgc ttt ctg acc gtg      960
Phe Ser Pro Gly Gly Thr Ser Thr Thr Asn Ile Arg Phe Leu Thr Val
305                 310                 315                 320 cgt acg ggc atc gac acn                                              978
Arg Thr Gly Ile Asp Thr
                325

<210> SEQ ID NO 4
<211> LENGTH: 326
<212> TYPE: PRT
<213> ORGANISM: Avian orthoreovirus

<400> SEQUENCE: 4

Met Ala Gly Leu Thr Pro Ser Gln Arg Arg Glu Val Val Gly Leu Ile
 1               5                  10                  15

Leu Ser Leu Thr Ser Asn Thr Ser Ile Gly Pro Gly Asp Leu Thr Pro
```

```
                    20                  25                  30
Ile Tyr Asp Arg Leu Ser Ala Val Glu Thr Ala Cys Ala Thr Leu Ser
                35                  40                  45

Asp Ser Val Gly Gln Leu Ala Ser Thr Thr Ser Ala Leu Ser Thr Arg
        50                  55                  60

Leu Asp Asn Leu Val Ser Val Ser Gln Asp Met Ala Asn Asp Leu Arg
65                  70                  75                  80

Asp Val Gln Ser Arg Val Ser Ala Leu Gln Thr Ser Ile Asp Ser Met
                85                  90                  95

Ser Ser Asp Ile Ser Thr Leu Ser Gln Ser Leu Ser Asn His Asp Ser
            100                 105                 110

Gln Ile Ser Thr Leu Ser Ser Val Ser Thr Val Ala Thr Asn Val
        115                 120                 125

Ser Asn Leu Gln Arg Asp Val Ala Ala Ser Ala Leu Asn Ile Ser Asp
    130                 135                 140

Leu Gln Arg Arg Val Ala Ala Leu Glu Ser Ser Pro Gly Ser Ser Leu
145                 150                 155                 160

Thr Phe Leu Ala Pro Leu Arg Ala Asp Gly Gly Ser Val Ser Leu Asp
                165                 170                 175

Met Asp Pro Tyr Phe Cys Ser Glu Arg Ala Asn Leu Thr Ser Tyr Ser
            180                 185                 190

Ala Ser Ala Gln Leu Leu Gln Phe Gln Trp Phe Val Arg Ser Glu Gly
        195                 200                 205

Gly Ser Ser Asp Ser Ile Asn Met Ser Val Val Ala His Cys His Gly
    210                 215                 220

Arg Arg Thr Asp Tyr Leu Met Ser Ser His Asp Ser Leu Thr Val Thr
225                 230                 235                 240

Gly Asn Ser Val Ser Leu Val Phe Asn Leu Asp Tyr Ile Thr Thr Ser
                245                 250                 255

Gly Val Asp Tyr Ala Arg Leu Ile Pro Cys His Gly Phe Gln Gln Ala
            260                 265                 270

Thr Phe Pro Val Asp Ile Ser Phe Thr Lys Asn Asp Thr Thr His Thr
        275                 280                 285

Tyr Gln Val Tyr Gly Ala Phe Asn Gly Pro Arg Val Phe Lys Val Thr
    290                 295                 300

Phe Ser Pro Gly Gly Thr Ser Thr Thr Asn Ile Arg Phe Leu Thr Val
305                 310                 315                 320

Arg Thr Gly Ile Asp Thr
                325

<210> SEQ ID NO 5
<211> LENGTH: 978
<212> TYPE: DNA
<213> ORGANISM: Avian orthoreovirus
<220> FEATURE:
<221> NAME/KEY: CDS
<222> LOCATION: (1)..(978)

<400> SEQUENCE: 5 atg gcc gga tta act ccc tca cag cga aga gaa gtc gtg gga ttg ata      48
Met Ala Gly Leu Thr Pro Ser Gln Arg Arg Glu Val Val Gly Leu Ile
1               5                   10                  15 ctc tcc ttg act tcg agc gcg aat aca aat tgt gga gat ttg acg ccc      96
Leu Ser Leu Thr Ser Ser Ala Asn Thr Asn Cys Gly Asp Leu Thr Pro
                20                  25                  30 gta tat gac cgt ttg ctt agt ctg gaa tcc act att acg tca ttg aat     144
Val Tyr Asp Arg Leu Leu Ser Leu Glu Ser Thr Ile Thr Ser Leu Asn
```

```
                        35                  40                  45
ggc tct gtt agc gac ttg tcg cgg aag gta tcg gat ctg gaa tct gat    192
Gly Ser Val Ser Asp Leu Ser Arg Lys Val Ser Asp Leu Glu Ser Asp
     50                  55                  60 ttg caa gac gtc att tca tct tta ggt cag gct aat tca acg ttg acc    240
Leu Gln Asp Val Ile Ser Ser Leu Gly Gln Ala Asn Ser Thr Leu Thr
 65                  70                  75                  80 gag tta tct aaa gaa cta cgt cag tta agt ggc tct gtt gac act ctc    288
Glu Leu Ser Lys Glu Leu Arg Gln Leu Ser Gly Ser Val Asp Thr Leu
                 85                  90                  95 gtc acg tct gtt tcg gat cta tcg acc act gta tcc ggg cat cag aac    336
Val Thr Ser Val Ser Asp Leu Ser Thr Thr Val Ser Gly His Gln Asn
            100                 105                 110 gcg ata gcc gct ata caa act tcc gtt cac gct aat acg act gac att    384
Ala Ile Ala Ala Ile Gln Thr Ser Val His Ala Asn Thr Thr Asp Ile
        115                 120                 125 agt aac ctg aaa agt agc ata tcg act atc ggc tta aat atc act gac    432
Ser Asn Leu Lys Ser Ser Ile Ser Thr Ile Gly Leu Asn Ile Thr Asp
130                 135                 140 cta gag caa cgt gtg gga aac atc gaa tca ggg tcg ggt cct act ttg    480
Leu Glu Gln Arg Val Gly Asn Ile Glu Ser Gly Ser Gly Pro Thr Leu
145                 150                 155                 160 aag ttt atg tca cct ctg agc ttg tcc caa ggc gta gcg tca ctg att    528
Lys Phe Met Ser Pro Leu Ser Leu Ser Gln Gly Val Ala Ser Leu Ile
                165                 170                 175 atg gat cct tac ttc tgt tca gac aat aag gcg cta acc tca tac tct    576
Met Asp Pro Tyr Phe Cys Ser Asp Asn Lys Ala Leu Thr Ser Tyr Ser
            180                 185                 190 aca gac gct cag ctg atg cag ttc cag tgg ctg gct cga ggt gag gat    624
Thr Asp Ala Gln Leu Met Gln Phe Gln Trp Leu Ala Arg Gly Glu Asp
        195                 200                 205 ggt tca tcg agc tct gtt gag atg ctt gtt aat gcg cac tgt cat ggg    672
Gly Ser Ser Ser Ser Val Glu Met Leu Val Asn Ala His Cys His Gly
210                 215                 220 cgt cgc act gac tat atg atg tcc act aca gag aat ttc act gtc acg    720
Arg Arg Thr Asp Tyr Met Met Ser Thr Thr Glu Asn Phe Thr Val Thr
225                 230                 235                 240 ggc aac tcc gta tcg ttg gtt ttc agt ctg gac tat att act aaa ccg    768
Gly Asn Ser Val Ser Leu Val Phe Ser Leu Asp Tyr Ile Thr Lys Pro
                245                 250                 255 cct tct gac ata tca cgt tta gta cca cgt gtc gga ttc cag gct gct    816
Pro Ser Asp Ile Ser Arg Leu Val Pro Arg Val Gly Phe Gln Ala Ala
            260                 265                 270 tcc ttt cct gtg gac gtc tct ttc act cgt gac gca act ccg cat gct    864
Ser Phe Pro Val Asp Val Ser Phe Thr Arg Asp Ala Thr Pro His Ala
        275                 280                 285 tac cag gta tac ggc gct ttt tct agc cct cgc gtc ttc aag atc acg    912
Tyr Gln Val Tyr Gly Ala Phe Ser Ser Pro Arg Val Phe Lys Ile Thr
290                 295                 300 ttc ctc aca ggt ggc act ggg act gcg aat ctc cgt ttc ttg acc gta    960
Phe Leu Thr Gly Gly Thr Gly Thr Ala Asn Leu Arg Phe Leu Thr Val
305                 310                 315                 320 cgt acg ggc atc gac acc                                            978
Arg Thr Gly Ile Asp Thr
                325

<210> SEQ ID NO 6
<211> LENGTH: 326
<212> TYPE: PRT
<213> ORGANISM: Avian orthoreovirus
```

<400> SEQUENCE: 6

```
Met Ala Gly Leu Thr Pro Ser Gln Arg Arg Glu Val Val Gly Leu Ile
1               5                   10                  15

Leu Ser Leu Thr Ser Ser Ala Asn Thr Asn Cys Gly Asp Leu Thr Pro
            20                  25                  30

Val Tyr Asp Arg Leu Leu Ser Leu Glu Ser Thr Ile Thr Ser Leu Asn
        35                  40                  45

Gly Ser Val Ser Asp Leu Ser Arg Lys Val Ser Asp Leu Glu Ser Asp
    50                  55                  60

Leu Gln Asp Val Ile Ser Ser Leu Gly Gln Ala Asn Ser Thr Leu Thr
65                  70                  75                  80

Glu Leu Ser Lys Glu Leu Arg Gln Leu Ser Gly Ser Val Asp Thr Leu
                85                  90                  95

Val Thr Ser Val Ser Asp Leu Ser Thr Thr Val Ser Gly His Gln Asn
            100                 105                 110

Ala Ile Ala Ala Ile Gln Thr Ser Val His Ala Asn Thr Thr Asp Ile
        115                 120                 125

Ser Asn Leu Lys Ser Ser Ile Ser Thr Ile Gly Leu Asn Ile Thr Asp
    130                 135                 140

Leu Glu Gln Arg Val Gly Asn Ile Glu Ser Gly Ser Gly Pro Thr Leu
145                 150                 155                 160

Lys Phe Met Ser Pro Leu Ser Leu Ser Gln Gly Val Ala Ser Leu Ile
                165                 170                 175

Met Asp Pro Tyr Phe Cys Ser Asp Asn Lys Ala Leu Thr Ser Tyr Ser
            180                 185                 190

Thr Asp Ala Gln Leu Met Gln Phe Gln Trp Leu Ala Arg Gly Glu Asp
        195                 200                 205

Gly Ser Ser Ser Val Glu Met Leu Val Asn Ala His Cys His Gly
    210                 215                 220

Arg Arg Thr Asp Tyr Met Met Ser Thr Thr Glu Asn Phe Thr Val Thr
225                 230                 235                 240

Gly Asn Ser Val Ser Leu Val Phe Ser Leu Asp Tyr Ile Thr Lys Pro
                245                 250                 255

Pro Ser Asp Ile Ser Arg Leu Val Pro Arg Val Gly Phe Gln Ala Ala
            260                 265                 270

Ser Phe Pro Val Asp Val Ser Phe Thr Arg Asp Ala Thr Pro His Ala
        275                 280                 285

Tyr Gln Val Tyr Gly Ala Phe Ser Ser Pro Arg Val Phe Lys Ile Thr
    290                 295                 300

Phe Leu Thr Gly Gly Thr Gly Thr Ala Asn Leu Arg Phe Leu Thr Val
305                 310                 315                 320

Arg Thr Gly Ile Asp Thr
                325
```

<210> SEQ ID NO 7
<211> LENGTH: 978
<212> TYPE: DNA
<213> ORGANISM: Avian orthoreovirus
<220> FEATURE:
<221> NAME/KEY: CDS
<222> LOCATION: (1)..(978)

<400> SEQUENCE: 7

```
atg gcc gga ctc act cca tca cag cga aga gaa gtc gtc ggg ctg ata     48
Met Ala Gly Leu Thr Pro Ser Gln Arg Arg Glu Val Val Gly Leu Ile
1               5                   10                  15
```

| | | |
|---|---|---|
| ctc tca ttg act tcg aac acg agt ata agt cct gga gat ttg aca ccg<br>Leu Ser Leu Thr Ser Asn Thr Ser Ile Ser Pro Gly Asp Leu Thr Pro<br>20 25 30 | 96 | |
| atc tac gat cgt ctc tcg gcc gtt gag aca gct tat tct act tta agc<br>Ile Tyr Asp Arg Leu Ser Ala Val Glu Thr Ala Tyr Ser Thr Leu Ser<br>35 40 45 | 144 | |
| gac tct gtg ggt caa ttg gct tca acg aca tct gct tta tct act cgt<br>Asp Ser Val Gly Gln Leu Ala Ser Thr Thr Ser Ala Leu Ser Thr Arg<br>50 55 60 | 192 | |
| ctg gat gac ttg gtg agt atg tca caa gat ata gta aat gac ttg agg<br>Leu Asp Asp Leu Val Ser Met Ser Gln Asp Ile Val Asn Asp Leu Arg<br>65 70 75 80 | 240 | |
| gat att caa agt cgt gta tct gca ttt caa ata tcg ata gat agt ctg<br>Asp Ile Gln Ser Arg Val Ser Ala Phe Gln Ile Ser Ile Asp Ser Leu<br>85 90 95 | 288 | |
| tcc agt gac att tcc acc cta tca cag tcg ctg tct aat cat gat tcc<br>Ser Ser Asp Ile Ser Thr Leu Ser Gln Ser Leu Ser Asn His Asp Ser<br>100 105 110 | 336 | |
| cag att tcc acg ctt tcc tct tct gtc ggc acg cta tcc act gac atg<br>Gln Ile Ser Thr Leu Ser Ser Ser Val Gly Thr Leu Ser Thr Asp Met<br>115 120 125 | 384 | |
| tcc aac ctc caa cgc gac gta act gca tct gca ctc aac att tct gat<br>Ser Asn Leu Gln Arg Asp Val Thr Ala Ser Ala Leu Asn Ile Ser Asp<br>130 135 140 | 432 | |
| ctt cag cga cgt gtt gct gct ctg gaa tcg agt tcc ggt tca ccc ctt<br>Leu Gln Arg Arg Val Ala Ala Leu Glu Ser Ser Ser Gly Ser Pro Leu<br>145 150 155 160 | 480 | |
| aca ttt ctt gct ccc ctg cga gct gat ggt ggc tcc gtc tcg tta gat<br>Thr Phe Leu Ala Pro Leu Arg Ala Asp Gly Gly Ser Val Ser Leu Asp<br>165 170 175 | 528 | |
| atg gat ccg tac ttt tgc tcg gaa agg gcg aac tta acg tct tac tca<br>Met Asp Pro Tyr Phe Cys Ser Glu Arg Ala Asn Leu Thr Ser Tyr Ser<br>180 185 190 | 576 | |
| gcg agt gcg cag ttg ctg cag ttt cag tgg ttt gtc agg agt gag gga<br>Ala Ser Ala Gln Leu Leu Gln Phe Gln Trp Phe Val Arg Ser Glu Gly<br>195 200 205 | 624 | |
| ggt tcc tca gac tca atc gac atg agc gtg gtg gct cac tgc cac ggc<br>Gly Ser Ser Asp Ser Ile Asp Met Ser Val Val Ala His Cys His Gly<br>210 215 220 | 672 | |
| cgt cgc acg gat tat ctg atg tct tcc cat gac tca ctc acc gtc act<br>Arg Arg Thr Asp Tyr Leu Met Ser Ser His Asp Ser Leu Thr Val Thr<br>225 230 235 240 | 720 | |
| ggc aac tca gtg tct cta gtg ttc aac ctg gat cac atc acc acg tct<br>Gly Asn Ser Val Ser Leu Val Phe Asn Leu Asp His Ile Thr Thr Ser<br>245 250 255 | 768 | |
| ggt gtg gat tat gct cgt ctg att ccg tgt cat ggt ttt caa caa gcc<br>Gly Val Asp Tyr Ala Arg Leu Ile Pro Cys His Gly Phe Gln Gln Ala<br>260 265 270 | 816 | |
| act ttt cct gtt gac atc tct ttc acg aaa aat gac act aca cac acg<br>Thr Phe Pro Val Asp Ile Ser Phe Thr Lys Asn Asp Thr Thr His Thr<br>275 280 285 | 864 | |
| tac caa gtc tat ggc gcg ttt gat ggc cct cgc gtc ttt aag gtg acc<br>Tyr Gln Val Tyr Gly Ala Phe Asp Gly Pro Arg Val Phe Lys Val Thr<br>290 295 300 | 912 | |
| ttc tct ccg ggt ggg acc agc acg acg agc gta cgt ttt ctg acc gtg<br>Phe Ser Pro Gly Gly Thr Ser Thr Thr Ser Val Arg Phe Leu Thr Val<br>305 310 315 320 | 960 | |
| cgt acg ggc atc gac acc<br>Arg Thr Gly Ile Asp Thr<br>325 | 978 | |

<210> SEQ ID NO 8
<211> LENGTH: 326
<212> TYPE: PRT
<213> ORGANISM: Avian orthoreovirus

<400> SEQUENCE: 8

Met Ala Gly Leu Thr Pro Ser Gln Arg Arg Glu Val Val Gly Leu Ile
1               5                   10                  15

Leu Ser Leu Thr Ser Asn Thr Ser Ile Ser Pro Gly Asp Leu Thr Pro
            20                  25                  30

Ile Tyr Asp Arg Leu Ser Ala Val Glu Thr Ala Tyr Ser Thr Leu Ser
        35                  40                  45

Asp Ser Val Gly Gln Leu Ala Ser Thr Thr Ser Ala Leu Ser Thr Arg
    50                  55                  60

Leu Asp Asp Leu Val Ser Met Ser Gln Asp Ile Val Asn Asp Leu Arg
65                  70                  75                  80

Asp Ile Gln Ser Arg Val Ser Ala Phe Gln Ile Ser Ile Asp Ser Leu
                85                  90                  95

Ser Ser Asp Ile Ser Thr Leu Ser Gln Ser Leu Ser Asn His Asp Ser
            100                 105                 110

Gln Ile Ser Thr Leu Ser Ser Val Gly Thr Leu Ser Thr Asp Met
        115                 120                 125

Ser Asn Leu Gln Arg Asp Val Thr Ala Ser Ala Leu Asn Ile Ser Asp
    130                 135                 140

Leu Gln Arg Arg Val Ala Ala Leu Glu Ser Ser Ser Gly Ser Pro Leu
145                 150                 155                 160

Thr Phe Leu Ala Pro Leu Arg Ala Asp Gly Gly Ser Val Ser Leu Asp
                165                 170                 175

Met Asp Pro Tyr Phe Cys Ser Glu Arg Ala Asn Leu Thr Ser Tyr Ser
            180                 185                 190

Ala Ser Ala Gln Leu Leu Gln Phe Gln Trp Phe Val Arg Ser Glu Gly
        195                 200                 205

Gly Ser Ser Asp Ser Ile Asp Met Ser Val Val Ala His Cys His Gly
    210                 215                 220

Arg Arg Thr Asp Tyr Leu Met Ser Ser His Asp Ser Leu Thr Val Thr
225                 230                 235                 240

Gly Asn Ser Val Ser Leu Val Phe Asn Leu Asp His Ile Thr Thr Ser
                245                 250                 255

Gly Val Asp Tyr Ala Arg Leu Ile Pro Cys His Gly Phe Gln Gln Ala
            260                 265                 270

Thr Phe Pro Val Asp Ile Ser Phe Thr Lys Asn Asp Thr Thr His Thr
        275                 280                 285

Tyr Gln Val Tyr Gly Ala Phe Asp Gly Pro Arg Val Phe Lys Val Thr
    290                 295                 300

Phe Ser Pro Gly Gly Thr Ser Thr Ser Val Arg Phe Leu Thr Val
305                 310                 315                 320

Arg Thr Gly Ile Asp Thr
                325

<210> SEQ ID NO 9
<211> LENGTH: 981
<212> TYPE: DNA
<213> ORGANISM: Avian orthoreovirus
<220> FEATURE:
<221> NAME/KEY: CDS
<222> LOCATION: (1)..(981)
<220> FEATURE:

<221> NAME/KEY: misc_feature
<222> LOCATION: (831)..(831)
<223> OTHER INFORMATION: y = c or t

<400> SEQUENCE: 9

```
atg gcc gga tta act ccc tcc cag cga aga gaa gtc gtg gga ttg ata     48
Met Ala Gly Leu Thr Pro Ser Gln Arg Arg Glu Val Val Gly Leu Ile
1               5                   10                  15 ctc tcc ttg act tcg agc gtg aat aca aac tgt gga gat ttg acg cct     96
Leu Ser Leu Thr Ser Ser Val Asn Thr Asn Cys Gly Asp Leu Thr Pro
            20                  25                  30 gta tat gac cgt ctg ctt agt ctg gaa tcc gct gtt gcg tcg ttg aat    144
Val Tyr Asp Arg Leu Leu Ser Leu Glu Ser Ala Val Ala Ser Leu Asn
        35                  40                  45 aac tct gta aat ggc ttg ttg cag aag gta tca gat ttc gag tct gat    192
Asn Ser Val Asn Gly Leu Leu Gln Lys Val Ser Asp Phe Glu Ser Asp
    50                  55                  60 ttg caa gac gtc act tca tcc cta ggc cag gcc aat tcg atg tta acc    240
Leu Gln Asp Val Thr Ser Ser Leu Gly Gln Ala Asn Ser Met Leu Thr
65                  70                  75                  80 gag cta tct aag gaa ctg cgt cag ttg agc agc tct gtt gac aat ctc    288
Glu Leu Ser Lys Glu Leu Arg Gln Leu Ser Ser Ser Val Asp Asn Leu
                85                  90                  95 gtc acg tcc gtt tct gat cta tcg acc gct gta tcc ggg cac cag aac    336
Val Thr Ser Val Ser Asp Leu Ser Thr Ala Val Ser Gly His Gln Asn
            100                 105                 110 gcc ata gcc gat ata caa gct tcc gtt cac gcc aat gca act gat att    384
Ala Ile Ala Asp Ile Gln Ala Ser Val His Ala Asn Ala Thr Asp Ile
        115                 120                 125 aac aac ctg aaa agc agt gtc tct act att agc tta aat atc act gat    432
Asn Asn Leu Lys Ser Ser Val Ser Thr Ile Ser Leu Asn Ile Thr Asp
    130                 135                 140 ctc gag caa cgc gtg gca aac atc gag tca ggg tca gac tct aat tta    480
Leu Glu Gln Arg Val Ala Asn Ile Glu Ser Gly Ser Asp Ser Asn Leu
145                 150                 155                 160 agg ttt gtg tca cct ctg aac ttg tcc caa ggc gtg gtg tca ttg atc    528
Arg Phe Val Ser Pro Leu Asn Leu Ser Gln Gly Val Val Ser Leu Ile
                165                 170                 175 atg gat cct tac ttc tgt tct gac aat aag gca cta acc tca tat tct    576
Met Asp Pro Tyr Phe Cys Ser Asp Asn Lys Ala Leu Thr Ser Tyr Ser
            180                 185                 190 acg gac gcg cag ctg atg cag ttt cag tgg ctg gct aga ggt gaa gat    624
Thr Asp Ala Gln Leu Met Gln Phe Gln Trp Leu Ala Arg Gly Glu Asp
        195                 200                 205 ggg tca tcg agc tct gtt gat atg ctc gtt aac gca cac tgt cat ggg    672
Gly Ser Ser Ser Ser Val Asp Met Leu Val Asn Ala His Cys His Gly
    210                 215                 220 cgt cgc act gac tat atg atg tcc act aca gag agt ttt act gtc acg    720
Arg Arg Thr Asp Tyr Met Met Ser Thr Thr Glu Ser Phe Thr Val Thr
225                 230                 235                 240 ggc aat tct gta tca ttg gtc ttc aat ctg gat tat atc acc aag ccg    768
Gly Asn Ser Val Ser Leu Val Phe Asn Leu Asp Tyr Ile Thr Lys Pro
                245                 250                 255 ccc tct gac atg tcg cgg cta gta ccc cgt gct gga ttc cag gct gct    816
Pro Ser Asp Met Ser Arg Leu Val Pro Arg Ala Gly Phe Gln Ala Ala
            260                 265                 270 tcg ttt ccc gtg gay gtc tcc ttc act cgt gac acg aca ccg cat gca    864
Ser Phe Pro Val Asp Val Ser Phe Thr Arg Asp Thr Thr Pro His Ala
        275                 280                 285 tac cag gtg tat ggt gct ttc tct agc cct cgc att ttt aag atc acg    912
Tyr Gln Val Tyr Gly Ala Phe Ser Ser Pro Arg Ile Phe Lys Ile Thr
```

```
                         290                 295                 300
ttc ctc aca ggt ggt act gga act gcg aat ctc cgt ttc ttg acc gtg         960
Phe Leu Thr Gly Gly Thr Gly Thr Ala Asn Leu Arg Phe Leu Thr Val
305                 310                 315                 320 cgt acg ggc atc gac act taa                                             981
Arg Thr Gly Ile Asp Thr
                325
```

<210> SEQ ID NO 10
<211> LENGTH: 326
<212> TYPE: PRT
<213> ORGANISM: Avian orthoreovirus

<400> SEQUENCE: 10

```
Met Ala Gly Leu Thr Pro Ser Gln Arg Arg Glu Val Val Gly Leu Ile
1               5                   10                  15

Leu Ser Leu Thr Ser Ser Val Asn Thr Asn Cys Gly Asp Leu Thr Pro
            20                  25                  30

Val Tyr Asp Arg Leu Leu Ser Leu Glu Ser Ala Val Ala Ser Leu Asn
        35                  40                  45

Asn Ser Val Asn Gly Leu Leu Gln Lys Val Ser Asp Phe Glu Ser Asp
    50                  55                  60

Leu Gln Asp Val Thr Ser Ser Leu Gly Gln Ala Asn Ser Met Leu Thr
65                  70                  75                  80

Glu Leu Ser Lys Glu Leu Arg Gln Leu Ser Ser Ser Val Asp Asn Leu
                85                  90                  95

Val Thr Ser Val Ser Asp Leu Ser Thr Ala Val Ser Gly His Gln Asn
            100                 105                 110

Ala Ile Ala Asp Ile Gln Ala Ser Val His Ala Asn Ala Thr Asp Ile
        115                 120                 125

Asn Asn Leu Lys Ser Ser Val Ser Thr Ile Ser Leu Asn Ile Thr Asp
    130                 135                 140

Leu Glu Gln Arg Val Ala Asn Ile Glu Ser Gly Ser Asp Ser Asn Leu
145                 150                 155                 160

Arg Phe Val Ser Pro Leu Asn Leu Ser Gln Gly Val Val Ser Leu Ile
                165                 170                 175

Met Asp Pro Tyr Phe Cys Ser Asp Asn Lys Ala Leu Thr Ser Tyr Ser
            180                 185                 190

Thr Asp Ala Gln Leu Met Gln Phe Gln Trp Leu Ala Arg Gly Glu Asp
        195                 200                 205

Gly Ser Ser Ser Val Asp Met Leu Val Asn Ala His Cys His Gly
    210                 215                 220

Arg Arg Thr Asp Tyr Met Met Ser Thr Thr Glu Ser Phe Thr Val Thr
225                 230                 235                 240

Gly Asn Ser Val Ser Leu Val Phe Asn Leu Asp Tyr Ile Thr Lys Pro
                245                 250                 255

Pro Ser Asp Met Ser Arg Leu Val Pro Arg Ala Gly Phe Gln Ala Ala
            260                 265                 270

Ser Phe Pro Val Asp Val Ser Phe Thr Arg Asp Thr Thr Pro His Ala
        275                 280                 285

Tyr Gln Val Tyr Gly Ala Phe Ser Ser Pro Arg Ile Phe Lys Ile Thr
    290                 295                 300

Phe Leu Thr Gly Gly Thr Gly Thr Ala Asn Leu Arg Phe Leu Thr Val
305                 310                 315                 320

Arg Thr Gly Ile Asp Thr
                325
```

```
<210> SEQ ID NO 11
<211> LENGTH: 981
<212> TYPE: DNA
<213> ORGANISM: Avian orthoreovirus
<220> FEATURE:
<221> NAME/KEY: CDS
<222> LOCATION: (1)..(981)

<400> SEQUENCE: 11 atg gcc gga ctc act cca tta cag cga aga gaa gtc gtc gga ctg ata        48
Met Ala Gly Leu Thr Pro Leu Gln Arg Arg Glu Val Val Gly Leu Ile
1               5                   10                  15 ctc tca ttg act tcg agc acg agt ata agt cct gga gat ttg aca cca        96
Leu Ser Leu Thr Ser Ser Thr Ser Ile Ser Pro Gly Asp Leu Thr Pro
            20                  25                  30 ata tat gat cgg ctg tcc gcc gtt gag acg atc tgc gac act cta agt       144
Ile Tyr Asp Arg Leu Ser Ala Val Glu Thr Ile Cys Asp Thr Leu Ser
        35                  40                  45 ggc tcc gtg ggc cag ttg acg act atg atg tct aat tta tct gct cgt       192
Gly Ser Val Gly Gln Leu Thr Thr Met Met Ser Asn Leu Ser Ala Arg
    50                  55                  60 ctg gat gat tta acg att gtc tcc cga gat atg gcc act gat ttg aga       240
Leu Asp Asp Leu Thr Ile Val Ser Arg Asp Met Ala Thr Asp Leu Arg
65                  70                  75                  80 aac gtc caa ggt agt gtg tct gcg ctt cga acg tca tta gat cat ctg       288
Asn Val Gln Gly Ser Val Ser Ala Leu Arg Thr Ser Leu Asp His Leu
                85                  90                  95 tcc ggt gat gtt tcc gct tta tct caa tca tta tcc gcc cat gat tca       336
Ser Gly Asp Val Ser Ala Leu Ser Gln Ser Leu Ser Ala His Asp Ser
            100                 105                 110 cag ctc tca aca ctc tcc gtc tct gtt agc gcc ctt tcg act gac gtg       384
Gln Leu Ser Thr Leu Ser Val Ser Val Ser Ala Leu Ser Thr Asp Val
        115                 120                 125 tct aac ctc aaa cgc gat gtg gca tca tct gcg ctc aat atc tct gac       432
Ser Asn Leu Lys Arg Asp Val Ala Ser Ser Ala Leu Asn Ile Ser Asp
    130                 135                 140 att cag cgg cgt gtc gcc gct ttg gaa tct ggt tct ggc gcg gtc cta       480
Ile Gln Arg Arg Val Ala Ala Leu Glu Ser Gly Ser Gly Ala Val Leu
145                 150                 155                 160 aca ttt cgt gct ccc ctt cgg ctc gat ggc gac tcc gtc tca tta gat       528
Thr Phe Arg Ala Pro Leu Arg Leu Asp Gly Asp Ser Val Ser Leu Asp
                165                 170                 175 atg gat cct tac ttt tgc tcg gaa agg gcg aac tta acg tca tac tcg       576
Met Asp Pro Tyr Phe Cys Ser Glu Arg Ala Asn Leu Thr Ser Tyr Ser
            180                 185                 190 gcg agc gcg cag ctg ttg cag ttt cag tgg ttt gtc agg agt gag gat       624
Ala Ser Ala Gln Leu Leu Gln Phe Gln Trp Phe Val Arg Ser Glu Asp
        195                 200                 205 ggt tct tcc gat tcg att gac atg agt gtc gtt gcc cat tgc cac ggt       672
Gly Ser Ser Asp Ser Ile Asp Met Ser Val Val Ala His Cys His Gly
    210                 215                 220 cgt cgt acg gat tac tta atg tcc tct cat gat tca ctc act gtc act       720
Arg Arg Thr Asp Tyr Leu Met Ser Ser His Asp Ser Leu Thr Val Thr
225                 230                 235                 240 ggt aac tcg gtc tct ctc gtg ttc aac tta gat tac atc aca tcg cct       768
Gly Asn Ser Val Ser Leu Val Phe Asn Leu Asp Tyr Ile Thr Ser Pro
                245                 250                 255 ggc gtg gat tat gct cgt ctg att cca tgt cat gga ttt caa caa gca       816
Gly Val Asp Tyr Ala Arg Leu Ile Pro Cys His Gly Phe Gln Gln Ala
            260                 265                 270
```

```
acc ttc ccc gtt gac att tcc ttc aca aaa agc gac gtt aca cac acg    864
Thr Phe Pro Val Asp Ile Ser Phe Thr Lys Ser Asp Val Thr His Thr
            275                 280                 285 tat cag gtc tat ggc gca ttc gat ggg cct cgt gtc ttc aaa gta acg    912
Tyr Gln Val Tyr Gly Ala Phe Asp Gly Pro Arg Val Phe Lys Val Thr
290                 295                 300 ttc tcg ccg ggt gaa act ggt gcg acg aat ata cga ttc ttg acc gtg    960
Phe Ser Pro Gly Glu Thr Gly Ala Thr Asn Ile Arg Phe Leu Thr Val
305                 310                 315                 320 cgt acg ggc atc gac acc taa                                        981
Arg Thr Gly Ile Asp Thr
            325

<210> SEQ ID NO 12
<211> LENGTH: 326
<212> TYPE: PRT
<213> ORGANISM: Avian orthoreovirus

<400> SEQUENCE: 12

Met Ala Gly Leu Thr Pro Leu Gln Arg Arg Glu Val Val Gly Leu Ile
1               5                   10                  15

Leu Ser Leu Thr Ser Ser Thr Ser Ile Ser Pro Gly Asp Leu Thr Pro
            20                  25                  30

Ile Tyr Asp Arg Leu Ser Ala Val Glu Thr Ile Cys Asp Thr Leu Ser
        35                  40                  45

Gly Ser Val Gly Gln Leu Thr Thr Met Met Ser Asn Leu Ser Ala Arg
    50                  55                  60

Leu Asp Asp Leu Thr Ile Val Ser Arg Asp Met Ala Thr Asp Leu Arg
65                  70                  75                  80

Asn Val Gln Gly Ser Val Ser Ala Leu Arg Thr Ser Leu Asp His Leu
                85                  90                  95

Ser Gly Asp Val Ser Ala Leu Ser Gln Ser Leu Ser Ala His Asp Ser
            100                 105                 110

Gln Leu Ser Thr Leu Ser Val Ser Val Ser Ala Leu Ser Thr Asp Val
        115                 120                 125

Ser Asn Leu Lys Arg Asp Val Ala Ser Ser Ala Leu Asn Ile Ser Asp
    130                 135                 140

Ile Gln Arg Arg Val Ala Ala Leu Glu Ser Gly Ser Gly Ala Val Leu
145                 150                 155                 160

Thr Phe Arg Ala Pro Leu Arg Leu Asp Gly Asp Ser Val Ser Leu Asp
                165                 170                 175

Met Asp Pro Tyr Phe Cys Ser Glu Arg Ala Asn Leu Thr Ser Tyr Ser
            180                 185                 190

Ala Ser Ala Gln Leu Leu Gln Phe Gln Trp Phe Val Arg Ser Glu Asp
        195                 200                 205

Gly Ser Ser Asp Ser Ile Asp Met Ser Val Val Ala His Cys His Gly
    210                 215                 220

Arg Arg Thr Asp Tyr Leu Met Ser Ser His Asp Ser Leu Thr Val Thr
225                 230                 235                 240

Gly Asn Ser Val Ser Leu Val Phe Asn Leu Asp Tyr Ile Thr Ser Pro
                245                 250                 255

Gly Val Asp Tyr Ala Arg Leu Ile Pro Cys His Gly Phe Gln Gln Ala
            260                 265                 270

Thr Phe Pro Val Asp Ile Ser Phe Thr Lys Ser Asp Val Thr His Thr
        275                 280                 285

Tyr Gln Val Tyr Gly Ala Phe Asp Gly Pro Arg Val Phe Lys Val Thr
    290                 295                 300
```

```
Phe Ser Pro Gly Glu Thr Gly Ala Thr Asn Ile Arg Phe Leu Thr Val
305                 310                 315                 320

Arg Thr Gly Ile Asp Thr
                325

<210> SEQ ID NO 13
<211> LENGTH: 978
<212> TYPE: DNA
<213> ORGANISM: Avian orthoreovirus
<220> FEATURE:
<221> NAME/KEY: CDS
<222> LOCATION: (1)..(978)

<400> SEQUENCE: 13 atg gaa ggt ctc aat cag tca cag cga aga gag gtc gtg ggg ctg ata      48
Met Glu Gly Leu Asn Gln Ser Gln Arg Arg Glu Val Val Gly Leu Ile
1               5                   10                  15 ctc tca ttg act tcg agc gtg act ata agt cct ggc gat ttg acg caa      96
Leu Ser Leu Thr Ser Ser Val Thr Ile Ser Pro Gly Asp Leu Thr Gln
                20                  25                  30 cta cgt gag cgt atc tcg gca tta gaa tct gct aac gcg tcg tta aat     144
Leu Arg Glu Arg Ile Ser Ala Leu Glu Ser Ala Asn Ala Ser Leu Asn
            35                  40                  45 gag gct att gaa ggc gtg tta act cag ttg gtg gat ttg tca cag aag     192
Glu Ala Ile Glu Gly Val Leu Thr Gln Leu Val Asp Leu Ser Gln Lys
        50                  55                  60 ctg agc aat gca gcg gac gct atg gtt gaa tta cga gga gag tta aat     240
Leu Ser Asn Ala Ala Asp Ala Met Val Glu Leu Arg Gly Glu Leu Asn
65                  70                  75                  80 tca ttg act gct agc gtt cag att atc cag tcc tct ttg aaa tca ctt     288
Ser Leu Thr Ala Ser Val Gln Ile Ile Gln Ser Ser Leu Lys Ser Leu
                85                  90                  95 aca gac agt atg tcg gat ctt tct gac cga acg act gct aat acc tcg     336
Thr Asp Ser Met Ser Asp Leu Ser Asp Arg Thr Thr Ala Asn Thr Ser
                100                 105                 110 tcg atc acg aat ctg gca agt aag gtg gat ggt ctt acg gtc gat gtg     384
Ser Ile Thr Asn Leu Ala Ser Lys Val Asp Gly Leu Thr Val Asp Val
            115                 120                 125 act aac ctt aag cgg gac gtg tca aat cag ggt ctt aaa gtt act agt     432
Thr Asn Leu Lys Arg Asp Val Ser Asn Gln Gly Leu Lys Val Thr Ser
        130                 135                 140 ctc gaa cag cgt gta tct agt tta gag tct ggc gtt ggt tct gtc cct     480
Leu Glu Gln Arg Val Ser Ser Leu Glu Ser Gly Val Gly Ser Val Pro
145                 150                 155                 160 aca ttt gct gct ccc ctc aaa ttg gaa agc ggg act gtc tct ctc gat     528
Thr Phe Ala Ala Pro Leu Lys Leu Glu Ser Gly Thr Val Ser Leu Asp
                165                 170                 175 tta gat cct tat ttt tgt tct gtg gac cat aat ctt acg tcg tat tcc     576
Leu Asp Pro Tyr Phe Cys Ser Val Asp His Asn Leu Thr Ser Tyr Ser
                180                 185                 190 gca agt gcg ata ttg atg aat ttt cag tgg ctt gtc cgc agt gag gga     624
Ala Ser Ala Ile Leu Met Asn Phe Gln Trp Leu Val Arg Ser Glu Gly
            195                 200                 205 gga tcg tct gac tcg ttt gat atg aat gtg aca gct cat agc cat ggc     672
Gly Ser Ser Asp Ser Phe Asp Met Asn Val Thr Ala His Ser His Gly
        210                 215                 220 cag agg aca gat tat atg atg tct act act cag tcg ttg act gtt act     720
Gln Arg Thr Asp Tyr Met Met Ser Thr Thr Gln Ser Leu Thr Val Thr
225                 230                 235                 240 ggg aat cct gtc acc cta gtc ttt gat ctt aac gct ctt att tcc ccg     768
Gly Asn Pro Val Thr Leu Val Phe Asp Leu Asn Ala Leu Ile Ser Pro
```

|   |   |   |   |   |   |   |   |   |   |   |   |   |   |   |   |     |
|---|---|---|---|---|---|---|---|---|---|---|---|---|---|---|---|-----|
|   |   | 245 |   |   |   | 250 |   |   |   | 255 |   |   |   |   |   |     |
| ccc | tcc | gat | tat | tct | cgc | tta | ata | cca | tgt | cat | ggc | ttc | caa | caa | gca | 816 |
| Pro | Ser | Asp | Tyr | Ser | Arg | Leu | Ile | Pro | Cys | His | Gly | Phe | Gln | Gln | Ala |     |
|   |   | 260 |   |   |   | 265 |   |   |   | 270 |   |   |   |   |   |     |
| acg | ttc | ccg | gtg | gat | ctt | tcc | ttc | aag | cgc | gat | gat | gtc | acg | cac | tca | 864 |
| Thr | Phe | Pro | Val | Asp | Leu | Ser | Phe | Lys | Arg | Asp | Asp | Val | Thr | His | Ser |     |
|   |   | 275 |   |   |   | 280 |   |   |   | 285 |   |   |   |   |   |     |
| tat | cag | gtg | tat | ggt | tcg | tat | aca | acc | cct | cgt | gtt | ttc | aag | ata | acc | 912 |
| Tyr | Gln | Val | Tyr | Gly | Ser | Tyr | Thr | Thr | Pro | Arg | Val | Phe | Lys | Ile | Thr |     |
|   |   | 290 |   |   |   | 295 |   |   |   | 300 |   |   |   |   |   |     |
| ttc | tct | cct | ggt | aac | cca | gtg | cct | gcg | gtc | ata | cgc | ttc | ata | acc | gtg | 960 |
| Phe | Ser | Pro | Gly | Asn | Pro | Val | Pro | Ala | Val | Ile | Arg | Phe | Ile | Thr | Val |     |
| 305 |   |   |   |   | 310 |   |   |   |   | 315 |   |   |   |   | 320 |     |
| cgt | acg | ggc | atc | gat | acc |   |   |   |   |   |   |   |   |   |   | 978 |
| Arg | Thr | Gly | Ile | Asp | Thr |   |   |   |   |   |   |   |   |   |   |     |
|   |   |   |   | 325 |   |   |   |   |   |   |   |   |   |   |   |     |

<210> SEQ ID NO 14
<211> LENGTH: 326
<212> TYPE: PRT
<213> ORGANISM: Avian orthoreovirus

<400> SEQUENCE: 14

Met Glu Gly Leu Asn Gln Ser Gln Arg Arg Glu Val Val Gly Leu Ile
1               5                   10                  15

Leu Ser Leu Thr Ser Ser Val Thr Ile Ser Pro Gly Asp Leu Thr Gln
                20                  25                  30

Leu Arg Glu Arg Ile Ser Ala Leu Glu Ser Ala Asn Ala Ser Leu Asn
            35                  40                  45

Glu Ala Ile Glu Gly Val Leu Thr Gln Leu Val Asp Leu Ser Gln Lys
        50                  55                  60

Leu Ser Asn Ala Ala Asp Ala Met Val Glu Leu Arg Gly Glu Leu Asn
65                  70                  75                  80

Ser Leu Thr Ala Ser Val Gln Ile Ile Gln Ser Ser Leu Lys Ser Leu
                85                  90                  95

Thr Asp Ser Met Ser Asp Leu Ser Asp Arg Thr Thr Ala Asn Thr Ser
            100                 105                 110

Ser Ile Thr Asn Leu Ala Ser Lys Val Asp Gly Leu Thr Val Asp Val
        115                 120                 125

Thr Asn Leu Lys Arg Asp Val Ser Asn Gln Gly Leu Lys Val Thr Ser
130                 135                 140

Leu Glu Gln Arg Val Ser Ser Leu Glu Ser Gly Val Gly Ser Val Pro
145                 150                 155                 160

Thr Phe Ala Ala Pro Leu Lys Leu Glu Ser Gly Thr Val Ser Leu Asp
                165                 170                 175

Leu Asp Pro Tyr Phe Cys Ser Val Asp His Asn Leu Thr Ser Tyr Ser
            180                 185                 190

Ala Ser Ala Ile Leu Met Asn Phe Gln Trp Leu Val Arg Ser Glu Gly
        195                 200                 205

Gly Ser Ser Asp Ser Phe Asp Met Asn Val Thr Ala His Ser His Gly
210                 215                 220

Gln Arg Thr Asp Tyr Met Met Ser Thr Thr Gln Ser Leu Thr Val Thr
225                 230                 235                 240

Gly Asn Pro Val Thr Leu Val Phe Asp Leu Asn Ala Leu Ile Ser Pro
                245                 250                 255

Pro Ser Asp Tyr Ser Arg Leu Ile Pro Cys His Gly Phe Gln Gln Ala
            260                 265                 270

```
Thr Phe Pro Val Asp Leu Ser Phe Lys Arg Asp Asp Val Thr His Ser
            275                 280                 285
Tyr Gln Val Tyr Gly Ser Tyr Thr Thr Pro Arg Val Phe Lys Ile Thr
        290                 295                 300
Phe Ser Pro Gly Asn Pro Val Pro Ala Val Ile Arg Phe Ile Thr Val
305                 310                 315                 320
Arg Thr Gly Ile Asp Thr
            325

<210> SEQ ID NO 15
<211> LENGTH: 969
<212> TYPE: DNA
<213> ORGANISM: Avian orthoreovirus
<220> FEATURE:
<221> NAME/KEY: CDS
<222> LOCATION: (1)..(969)
<220> FEATURE:
<221> NAME/KEY: misc_feature
<222> LOCATION: (968)..(969)
<223> OTHER INFORMATION: n = a, c, g or t

<400> SEQUENCE: 15 atg gaa ggg tta act cag tca caa cga aga gaa gtc gtg ggg ctg ata      48
Met Glu Gly Leu Thr Gln Ser Gln Arg Arg Glu Val Val Gly Leu Ile
1               5                   10                  15 ctc tct ttg act tcg agc gcg aat ata agc act gga gat tta gct cag      96
Leu Ser Leu Thr Ser Ser Ala Asn Ile Ser Thr Gly Asp Leu Ala Gln
            20                  25                  30 att cgt agc cgc cta tcg gcg ttg gaa tca tcc aat gcg tca ttg agt     144
Ile Arg Ser Arg Leu Ser Ala Leu Glu Ser Ser Asn Ala Ser Leu Ser
        35                  40                  45 gag act gta aat ggt gcg gtg agt cag tta gta gtc ttg tct tcg cga     192
Glu Thr Val Asn Gly Ala Val Ser Gln Leu Val Val Leu Ser Ser Arg
    50                  55                  60 atc gac aat cta gcc gct act gtg gct gat gga cag ctg gaa ttg cgc     240
Ile Asp Asn Leu Ala Ala Thr Val Ala Asp Gly Gln Leu Glu Leu Arg
65                  70                  75                  80 tct ttg gtc atg gat gtt aag aat atc cga tcg tta tta gat gat gtc     288
Ser Leu Val Met Asp Val Lys Asn Ile Arg Ser Leu Leu Asp Asp Val
                85                  90                  95 tct acg acc gtg gta tct tta tcc gct tca gtt cgc gaa cat gac tca     336
Ser Thr Thr Val Val Ser Leu Ser Ala Ser Val Arg Glu His Asp Ser
            100                 105                 110 tca att att gat tta agg cgt cag ttc ggt ttg ctt tcc acc gat aca     384
Ser Ile Ile Asp Leu Arg Arg Gln Phe Gly Leu Leu Ser Thr Asp Thr
        115                 120                 125 gcc aat ctt aaa gct gat gtt gcc gct cag tcc ctc ata gtc act agt     432
Ala Asn Leu Lys Ala Asp Val Ala Ala Gln Ser Leu Ile Val Thr Ser
    130                 135                 140 ctt gag cag cgt gtt act gcc cta gaa tct agt acc ggc tcc ctc cct     480
Leu Glu Gln Arg Val Thr Ala Leu Glu Ser Ser Thr Gly Ser Leu Pro
145                 150                 155                 160 tcg ttc tcc gcc cca ctc aaa cta gat gat ggg acc gtt tca tta gac     528
Ser Phe Ser Ala Pro Leu Lys Leu Asp Asp Gly Thr Val Ser Leu Asp
                165                 170                 175 tta gat cct tac ttc tgy tcg gtg gat cat aat cta aca tct tat tct     576
Leu Asp Pro Tyr Phe Cys Ser Val Asp His Asn Leu Thr Ser Tyr Ser
            180                 185                 190 gcc agt gcg cag tta atg caa ttc caa tgg ttc gtg aga ggt gag gga     624
Ala Ser Ala Gln Leu Met Gln Phe Gln Trp Phe Val Arg Gly Glu Gly
        195                 200                 205
```

```
ggt tca tct gat tcc ata gat atg agc gtc act gct cat tgc cac ggc    672
Gly Ser Ser Asp Ser Ile Asp Met Ser Val Thr Ala His Cys His Gly
    210                 215                 220 cgg cgg act gat tac atg atg tcc acc act caa tcc cta act gtt act    720
Arg Arg Thr Asp Tyr Met Met Ser Thr Thr Gln Ser Leu Thr Val Thr
225                 230                 235                 240 ggt acc tcc gtg tcc ctt gtc ttt gat tta aat aca ctc gtt act cca    768
Gly Thr Ser Val Ser Leu Val Phe Asp Leu Asn Thr Leu Val Thr Pro
                245                 250                 255 cct tct gac tac tcg cgc ctt att ccg tgt cat ggg ttc cag cag gca    816
Pro Ser Asp Tyr Ser Arg Leu Ile Pro Cys His Gly Phe Gln Gln Ala
            260                 265                 270 aca ttt cca gtt gat ctt tcg ttc aaa agg gat gaa gag aca cac tct    864
Thr Phe Pro Val Asp Leu Ser Phe Lys Arg Asp Glu Glu Thr His Ser
        275                 280                 285 tat cag gta tat ggt tca tac tcg acg ccc gcg tgt ctt aag gtg act    912
Tyr Gln Val Tyr Gly Ser Tyr Ser Thr Pro Ala Cys Leu Lys Val Thr
    290                 295                 300 ttc tcc ccc tgg ggc ttc cag tta ccg gca gtc att cga ttc cta acc    960
Phe Ser Pro Trp Gly Phe Gln Leu Pro Ala Val Ile Arg Phe Leu Thr
305                 310                 315                 320 ctg cga cnn                                                        969
Leu Arg Xaa
```

<210> SEQ ID NO 16
<211> LENGTH: 323
<212> TYPE: PRT
<213> ORGANISM: Avian orthoreovirus
<220> FEATURE:
<221> NAME/

```
Ala Ser Ala Gln Leu Met Gln Phe Gln Trp Phe Val Arg Gly Glu Gly
        195                 200                 205

Gly Ser Ser Asp Ser Ile Asp Met Ser Val Thr Ala His Cys His Gly
    210                 215                 220

Arg Arg Thr Asp Tyr Met Met Ser Thr Thr Gln Ser Leu Thr Val Thr
225                 230                 235                 240

Gly Thr Ser Val Ser Leu Val Phe Asp Leu Asn Thr Leu Val Thr Pro
                245                 250                 255

Pro Ser Asp Tyr Ser Arg Leu Ile Pro Cys His Gly Phe Gln Gln Ala
            260                 265                 270

Thr Phe Pro Val Asp Leu Ser Phe Lys Arg Asp Glu Thr His Ser
        275                 280                 285

Tyr Gln Val Tyr Gly Ser Tyr Ser Thr Pro Ala Cys Leu Lys Val Thr
    290                 295                 300

Phe Ser Pro Trp Gly Phe Gln Leu Pro Ala Val Ile Arg Phe Leu Thr
305                 310                 315                 320

Leu Arg Xaa

<210> SEQ ID NO 17
<211> LENGTH: 966
<212> TYPE: DNA
<213> ORGANISM: Avian orthoreovirus
<220> FEATURE:
<221> NAME/KEY: CDS
<222> LOCATION: (1)..(966)

<400> SEQUENCE: 17 atg gca gga tta act ccc tta cag cga aga gaa gtc gtg ggc ttg ata      48
Met Ala Gly Leu Thr Pro Leu Gln Arg Arg Glu Val Val Gly Leu Ile
1               5                   10                  15 ctc tcc ttg act tcg agc gcg aat aca aac agt gga gat ttg acg ccc      96
Leu Ser Leu Thr Ser Ser Ala Asn Thr Asn Ser Gly Asp Leu Thr Pro
                20                  25                  30 ata tat gac cgt ctg ctt agt atg gag tcc gcc gtt gcg tca ttg agc     144
Ile Tyr Asp Arg Leu Leu Ser Met Glu Ser Ala Val Ala Ser Leu Ser
            35                  40                  45 gct tcc gtt agc ggc tta ttg cag aaa gta tca gat ttg gac tct gat     192
Ala Ser Val Ser Gly Leu Leu Gln Lys Val Ser Asp Leu Asp Ser Asp
        50                  55                  60 ttg cag aat gtc act tca tcc tta ggc cag gct gat tcg gcg ttg acc     240
Leu Gln Asn Val Thr Ser Ser Leu Gly Gln Ala Asp Ser Ala Leu Thr
65                  70                  75                  80 gca ttg tcc aag gaa ctg cac cag ttg agc agc tct att gaa aat gtc     288
Ala Leu Ser Lys Glu Leu His Gln Leu Ser Ser Ser Ile Glu Asn Val
                85                  90                  95 tca acg tct gtt tca gat gtg tcg act act gta tca ggg cat cag gct     336
Ser Thr Ser Val Ser Asp Val Ser Thr Thr Val Ser Gly His Gln Ala
            100                 105                 110 gcg ata gcc gcc gta caa act tcc gtt cac gct aat acg act gac att     384
Ala Ile Ala Ala Val Gln Thr Ser Val His Ala Asn Thr Thr Asp Ile
        115                 120                 125 agc aat ctg aaa agc agt gta tct act atc agc tta aat ctc gct gat     432
Ser Asn Leu Lys Ser Ser Val Ser Thr Ile Ser Leu Asn Leu Ala Asp
    130                 135                 140 ctt gaa cga cgt gta gac gac att gga tca ggt tca ggt tcc aac ctg     480
Leu Glu Arg Arg Val Asp Asp Ile Gly Ser Gly Ser Gly Ser Asn Leu
145                 150                 155                 160 agg ttt tcg tcc ccg ctg agt ttg tcc cag ggt gtg gtg tca ctg atc     528
Arg Phe Ser Ser Pro Leu Ser Leu Ser Gln Gly Val Val Ser Leu Ile
                165                 170                 175
```

```
atg gat cct tac ttc tgc tcg gac aat cag gcg tta acc tcg tat tcc    576
Met Asp Pro Tyr Phe Cys Ser Asp Asn Gln Ala Leu Thr Ser Tyr Ser
        180                 185                 190 aca gac gcg cag ttg atg caa ttc cag tgg cta gct aga ggt gag ggt    624
Thr Asp Ala Gln Leu Met Gln Phe Gln Trp Leu Ala Arg Gly Glu Gly
            195                 200                 205 ggc tca tcg agt tcc gtc gaa atg ctc gtc aat gca cat tgt cat gga    672
Gly Ser Ser Ser Ser Val Glu Met Leu Val Asn Ala His Cys His Gly
210                 215                 220 cgc cgt acc gat tat atg atg tcc act aca gaa aac ttc acc gtt aca    720
Arg Arg Thr Asp Tyr Met Met Ser Thr Thr Glu Asn Phe Thr Val Thr
225                 230                 235                 240 gat aac tct gtg tca ctg gtt ttc aat cta gac tat att act aaa cca    768
Asp Asn Ser Val Ser Leu Val Phe Asn Leu Asp Tyr Ile Thr Lys Pro
                245                 250                 255 cct tct gat atg tcg cgc ttg ata cca cgc gct ggg ttc cag gcc gct    816
Pro Ser Asp Met Ser Arg Leu Ile Pro Arg Ala Gly Phe Gln Ala Ala
            260                 265                 270 tct ttt ccc gtg gac gtc tcc ttc acc cgt gac acg aca acg cac gct    864
Ser Phe Pro Val Asp Val Ser Phe Thr Arg Asp Thr Thr Thr His Ala
        275                 280                 285 tac cag gtg tat ggt act ttt tct agt cct cgc att ttt aag atc aca    912
Tyr Gln Val Tyr Gly Thr Phe Ser Ser Pro Arg Ile Phe Lys Ile Thr
    290                 295                 300 ttt ctt aca ggt ggt act gga acc tgc aaa cat tcg ttt ctt gag ccg    960
Phe Leu Thr Gly Gly Thr Gly Thr Cys Lys His Ser Phe Leu Glu Pro
305                 310                 315                 320 gcg acg                                                            966
Ala Thr

<210> SEQ ID NO 18
<211> LENGTH: 322
<212> TYPE: PRT
<213> ORGANISM: Avian orthoreovirus

<400> SEQUENCE: 18

Met Ala Gly Leu Thr Pro Leu Gln Arg Arg Glu Val Val Gly Leu Ile
1               5                   10                  15

Leu Ser Leu Thr Ser Ser Ala Asn Thr Asn Ser Gly Asp Leu Thr Pro
            20                  25                  30

Ile Tyr Asp Arg Leu Leu Ser Met Glu Ser Ala Val Ala Ser Leu Ser
        35                  40                  45

Ala Ser Val Ser Gly Leu Leu Gln Lys Val Ser Asp Leu Asp Ser Asp
    50                  55                  60

Leu Gln Asn Val Thr Ser Ser Leu Gly Gln Ala Asp Ser Ala Leu Thr
65                  70                  75                  80

Ala Leu Ser Lys Glu Leu His Gln Leu Ser Ser Ser Ile Glu Asn Val
                85                  90                  95

Ser Thr Ser Val Ser Asp Val Ser Thr Thr Val Ser Gly His Gln Ala
            100                 105                 110

Ala Ile Ala Ala Val Gln Thr Ser Val His Ala Asn Thr Thr Asp Ile
        115                 120                 125

Ser Asn Leu Lys Ser Ser Val Ser Thr Ile Ser Leu Asn Leu Ala Asp
    130                 135                 140

Leu Glu Arg Arg Val Asp Asp Ile Gly Ser Gly Ser Gly Ser Asn Leu
145                 150                 155                 160

Arg Phe Ser Ser Pro Leu Ser Leu Ser Gln Gly Val Val Ser Leu Ile
                165                 170                 175
```

```
Met Asp Pro Tyr Phe Cys Ser Asp Asn Gln Ala Leu Thr Ser Tyr Ser
            180                 185                 190

Thr Asp Ala Gln Leu Met Gln Phe Gln Trp Leu Ala Arg Gly Glu Gly
        195                 200                 205

Gly Ser Ser Ser Val Glu Met Leu Val Asn Ala His Cys His Gly
    210                 215                 220

Arg Arg Thr Asp Tyr Met Met Ser Thr Thr Glu Asn Phe Thr Val Thr
225                 230                 235                 240

Asp Asn Ser Val Ser Leu Val Phe Asn Leu Asp Tyr Ile Thr Lys Pro
                245                 250                 255

Pro Ser Asp Met Ser Arg Leu Ile Pro Arg Ala Gly Phe Gln Ala Ala
            260                 265                 270

Ser Phe Pro Val Asp Val Ser Phe Thr Arg Asp Thr Thr His Ala
        275                 280                 285

Tyr Gln Val Tyr Gly Thr Phe Ser Ser Pro Arg Ile Phe Lys Ile Thr
    290                 295                 300

Phe Leu Thr Gly Gly Thr Gly Thr Cys Lys His Ser Phe Leu Glu Pro
305                 310                 315                 320

Ala Thr

<210> SEQ ID NO 19
<211> LENGTH: 960
<212> TYPE: DNA
<213> ORGANISM: Avian orthoreovirus
<220> FEATURE:
<221> NAME/KEY: CDS
<222> LOCATION: (1)..(960)
<220> FEATURE:
<221> NAME/KEY: misc_feature
<222> LOCATION: (960)..(960)
<223> OTHER INFORMATION: n = a, c, g or t

<400> SEQUENCE: 19 atg gcc gga ctc act cca tca cag cga aga gaa gtc gtc ggg atg ata      48
Met Ala Gly Leu Thr Pro Ser Gln Arg Arg Glu Val Val Gly Met Ile
1               5                   10                  15 ctc tca ttg act tcg agc acg agt ata agt cct gga gat ttg gca cca     96
Leu Ser Leu Thr Ser Ser Thr Ser Ile Ser Pro Gly Asp Leu Ala Pro
                20                  25                  30 ata tac gat cgc ctc tct gcc gtt gag acg att tgc gcc acc tta agt    144
Ile Tyr Asp Arg Leu Ser Ala Val Glu Thr Ile Cys Ala Thr Leu Ser
            35                  40                  45 gac tct gtg agt cag ctg att tca aag acg tct gat cta tct aat cgt    192
Asp Ser Val Ser Gln Leu Ile Ser Lys Thr Ser Asp Leu Ser Asn Arg
        50                  55                  60 tta aat ggc ttg gtg aat gtg tcc caa gat ata gct aac gac tta aga    240
Leu Asn Gly Leu Val Asn Val Ser Gln Asp Ile Ala Asn Asp Leu Arg
65                  70                  75                  80 gat att caa agt cgt gtg tct gca ctt caa aca ttg gta gat ggt gtg    288
Asp Ile Gln Ser Arg Val Ser Ala Leu Gln Thr Leu Val Asp Gly Val
                85                  90                  95 tcc agt gat gtt tct ctc cta tca cag tcg ttg tct gct cac gat tca    336
Ser Ser Asp Val Ser Leu Leu Ser Gln Ser Leu Ser Ala His Asp Ser
                100                 105                 110 cag ctc tcc gag ctt tcc tct tcg gtt agc act ctg tct act gac atg    384
Gln Leu Ser Glu Leu Ser Ser Ser Val Ser Thr Leu Ser Thr Asp Met
            115                 120                 125 tca aac ctt caa cgt gat gtg act gca tct gca ctc aat att tct gat    432
Ser Asn Leu Gln Arg Asp Val Thr Ala Ser Ala Leu Asn Ile Ser Asp
        130                 135                 140
```

```
ctt cag caa cgt gtc gcc ggt ttg gaa tcg agc tct ggg tca tct ctc        480
Leu Gln Gln Arg Val Ala Gly Leu Glu Ser Ser Ser Gly Ser Ser Leu
145                 150                 155                 160 acg ttc ctt gct cca ctt cgg gtt gat gga ggt tcc gtc tcg ttg gac        528
Thr Phe Leu Ala Pro Leu Arg Val Asp Gly Gly Ser Val Ser Leu Asp
                165                 170                 175 atg gat ccg tac ttt tgc tcc gaa agg tcg aac tta aca tcc tac tcg        576
Met Asp Pro Tyr Phe Cys Ser Glu Arg Ser Asn Leu Thr Ser Tyr Ser
            180                 185                 190 gcg agc gca cag ttg ttg cag ttt cag tgg tac gtt agg agt gag ggt        624
Ala Ser Ala Gln Leu Leu Gln Phe Gln Trp Tyr Val Arg Ser Glu Gly
        195                 200                 205 ggc tct tca gat tcg att gac atg agc gtg gtg gct cat tgc cac ggt        672
Gly Ser Ser Asp Ser Ile Asp Met Ser Val Val Ala His Cys His Gly
    210                 215                 220 cgt cgc acg gat tat ttg atg tcc act cat gat tcg ctc acc gtc act        720
Arg Arg Thr Asp Tyr Leu Met Ser Thr His Asp Ser Leu Thr Val Thr
225                 230                 235                 240 ggc aac tca gtg tcc tta gta ttc aat cta gac tac atc acc acg tct        768
Gly Asn Ser Val Ser Leu Val Phe Asn Leu Asp Tyr Ile Thr Thr Ser
                245                 250                 255 ggt gtg gag tac gct cgt ctg atc ccg agt cat ggt ttc caa cag gct        816
Gly Val Glu Tyr Ala Arg Leu Ile Pro Ser His Gly Phe Gln Gln Ala
            260                 265                 270 act ttt ccc gtt gat atc tct ttc acg aga aat gac acc aca cat acg        864
Thr Phe Pro Val Asp Ile Ser Phe Thr Arg Asn Asp Thr Thr His Thr
        275                 280                 285 tac caa gtt tat ggt gca ttt gat ggc cct cgc gtg ttt aaa gta aca        912
Tyr Gln Val Tyr Gly Ala Phe Asp Gly Pro Arg Val Phe Lys Val Thr
    290                 295                 300 ttc tcg ccg ggc gag aac cag cac gac caa atg tgc gat tca acc gan        960
Phe Ser Pro Gly Glu Asn Gln His Asp Gln Met Cys Asp Ser Thr Xaa
305                 310                 315                 320

<210> SEQ ID NO 20
<211> LENGTH: 320
<212> TYPE: PRT
<213> ORGANISM: Avian orthoreovirus
<220> FEATURE:
<221> NAME/KEY: misc_feature
<222> LOCATION: (320)..(320)
<223> OTHER INFORMATION: The 'Xaa' at location 320 stands for Glu, or
      Asp.

<400> SEQUENCE: 20

Met Ala Gly Leu Thr Pro Ser Gln Arg Arg Glu Val Val Gly Met Ile
1               5                   10                  15

Leu Ser Leu Thr Ser Ser Thr Ser Ile Ser Pro Gly Asp Leu Ala Pro
                20                  25                  30

Ile Tyr Asp Arg Leu Ser Ala Val Glu Thr Ile Cys Ala Thr Leu Ser
            35                  40                  45

Asp Ser Val Ser Gln Leu Ile Ser Lys Thr Ser Asp Leu Ser Asn Arg
        50                  55                  60

Leu Asn Gly Leu Val Asn Val Ser Gln Asp Ile Ala Asn Asp Leu Arg
65                  70                  75                  80

Asp Ile Gln Ser Arg Val Ser Ala Leu Gln Thr Leu Val Asp Gly Val
                85                  90                  95

Ser Ser Asp Val Ser Leu Leu Ser Gln Ser Leu Ser Ala His Asp Ser
            100                 105                 110

Gln Leu Ser Glu Leu Ser Ser Ser Val Ser Thr Leu Ser Thr Asp Met
```

```
                   115                 120                 125
Ser Asn Leu Gln Arg Asp Val Thr Ala Ser Ala Leu Asn Ile Ser Asp
            130                 135                 140

Leu Gln Gln Arg Val Ala Gly Leu Glu Ser Ser Gly Ser Ser Leu
145                 150                 155                 160

Thr Phe Leu Ala Pro Leu Arg Val Asp Gly Ser Val Ser Leu Asp
                165                 170                 175

Met Asp Pro Tyr Phe Cys Ser Glu Arg Ser Asn Leu Thr Ser Tyr Ser
            180                 185                 190

Ala Ser Ala Gln Leu Leu Gln Phe Gln Trp Tyr Val Arg Ser Glu Gly
        195                 200                 205

Gly Ser Ser Asp Ser Ile Asp Met Ser Val Val Ala His Cys His Gly
    210                 215                 220

Arg Arg Thr Asp Tyr Leu Met Ser Thr His Asp Ser Leu Thr Val Thr
225                 230                 235                 240

Gly Asn Ser Val Ser Leu Val Phe Asn Leu Asp Tyr Ile Thr Thr Ser
                245                 250                 255

Gly Val Glu Tyr Ala Arg Leu Ile Pro Ser His Gly Phe Gln Gln Ala
            260                 265                 270

Thr Phe Pro Val Asp Ile Ser Phe Thr Arg Asn Asp Thr Thr His Thr
        275                 280                 285

Tyr Gln Val Tyr Gly Ala Phe Asp Gly Pro Arg Val Phe Lys Val Thr
    290                 295                 300

Phe Ser Pro Gly Glu Asn Gln His Asp Gln Met Cys Asp Ser Thr Xaa
305                 310                 315                 320

<210> SEQ ID NO 21
<211> LENGTH: 963
<212> TYPE: DNA
<213> ORGANISM: Avian orthoreovirus
<220> FEATURE:
<221> NAME/KEY: CDS
<222> LOCATION: (1)..(963)

<400> SEQUENCE: 21 atg gaa ggc tta act cag tca cag cga aga gag gtc gtg ggg ctg ata        48
Met Glu Gly Leu Thr Gln Ser Gln Arg Arg Glu Val Val Gly Leu Ile
1               5                   10                  15 ctc tca ttg act tcg agc gtg act aca agt cct ggc gat ttg acg gaa        96
Leu Ser Leu Thr Ser Ser Val Thr Thr Ser Pro Gly Asp Leu Thr Glu
            20                  25                  30 ctg cgt gaa cgc gtc tca gcg tta gaa tct gcc act gcg tcc ttg aat       144
Leu Arg Glu Arg Val Ser Ala Leu Glu Ser Ala Thr Ala Ser Leu Asn
        35                  40                  45 gag act ata aaa ggc gtg ttg ggc caa ttg gta gat ttg gca cag aag       192
Glu Thr Ile Lys Gly Val Leu Gly Gln Leu Val Asp Leu Ala Gln Lys
    50                  55                  60 ttg agt aat gcg gca gac gct ata gtc ggg ttg cga gga gag ttg aac       240
Leu Ser Asn Ala Ala Asp Ala Ile Val Gly Leu Arg Gly Glu Leu Asn
65                  70                  75                  80 tca tta gct gct agc gtc caa act att caa tct tct ttg aga tca ctt       288
Ser Leu Ala Ala Ser Val Gln Thr Ile Gln Ser Ser Leu Arg Ser Leu
                85                  90                  95 aca gac agt gtg tcg gat ctt tct ggc caa gtg act act aat gcg tcg       336
Thr Asp Ser Val Ser Asp Leu Ser Gly Gln Val Thr Thr Asn Ala Ser
            100                 105                 110 tcg atc acg aat gtg aag ggt atg ttg gat ggt ctt acg gtc gac gtg       384
Ser Ile Thr Asn Val Lys Gly Met Leu Asp Gly Leu Thr Val Asp Val
        115                 120                 125
```

```
gct aat ctt aag cgt gac gca tca aat cag ggt ctt aaa att act gat     432
Ala Asn Leu Lys Arg Asp Ala Ser Asn Gln Gly Leu Lys Ile Thr Asp
    130                 135                 140 ctc gag cag cgt gta gct ggt tta gag tct ggt tct gga tct att ccc     480
Leu Glu Gln Arg Val Ala Gly Leu Glu Ser Gly Ser Gly Ser Ile Pro
145                 150                 155                 160 aca ttc gcc gct cct ctt aag tta gac agc ggg att gta tca ctc gac     528
Thr Phe Ala Ala Pro Leu Lys Leu Asp Ser Gly Ile Val Ser Leu Asp
                165                 170                 175 ctg gat cct tac ttt tgt tcc gta gat cat aat ctt acg tcg tat tcc     576
Leu Asp Pro Tyr Phe Cys Ser Val Asp His Asn Leu Thr Ser Tyr Ser
                    180                 185                 190 gcc agt gcg tca tta atg aat ttc cag tgg ctt gtt cga ggt gag gga     624
Ala Ser Ala Ser Leu Met Asn Phe Gln Trp Leu Val Arg Gly Glu Gly
                195                 200                 205 gga tct tct gac tca ttc gat atg aat gta aca gct cat agc cat ggc     672
Gly Ser Ser Asp Ser Phe Asp Met Asn Val Thr Ala His Ser His Gly
210                 215                 220 cag agg acg gac tat atg atg tct act act caa tca ttg act gtt act     720
Gln Arg Thr Asp Tyr Met Met Ser Thr Thr Gln Ser Leu Thr Val Thr
225                 230                 235                 240 gga aat tca gtc acc ctg gtc ttt gac ctt aac gct ctt atc tct ccg     768
Gly Asn Ser Val Thr Leu Val Phe Asp Leu Asn Ala Leu Ile Ser Pro
                245                 250                 255 cca tct gat tat tct cgc ttg ata cca tgt cat ggt ttc caa caa gca     816
Pro Ser Asp Tyr Ser Arg Leu Ile Pro Cys His Gly Phe Gln Gln Ala
                260                 265                 270 acg ttt cca gta gac ctt tca ttt aag cga gat gac gtc aca cac tca     864
Thr Phe Pro Val Asp Leu Ser Phe Lys Arg Asp Asp Val Thr His Ser
                275                 280                 285 tat cag gtg tat ggt tcg tac acg act cct cgc gtt ttc aag ata acc     912
Tyr Gln Val Tyr Gly Ser Tyr Thr Thr Pro Arg Val Phe Lys Ile Thr
290                 295                 300 ttc tct cct ggc aat cca gtg cct gca gtc ata cgc ttc ata acc ggc     960
Phe Ser Pro Gly Asn Pro Val Pro Ala Val Ile Arg Phe Ile Thr Gly
305                 310                 315                 320 gac                                                                 963
Asp

<210> SEQ ID NO 22
<211> LENGTH: 321
<212> TYPE: PRT
<213> ORGANISM: Avian orthoreovirus

<400> SEQUENCE: 22

Met Glu Gly Leu Thr Gln Ser Gln Arg Arg Glu Val Val Gly Leu Ile
1               5                   10                  15

Leu Ser Leu Thr Ser Ser Val Thr Thr Ser Pro Gly Asp Leu Thr Glu
            20                  25                  30

Leu Arg Glu Arg Val Ser Ala Leu Glu Ser Ala Thr Ala Ser Leu Asn
        35                  40                  45

Glu Thr Ile Lys Gly Val Leu Gly Gln Leu Val Asp Leu Ala Gln Lys
    50                  55                  60

Leu Ser Asn Ala Ala Asp Ala Ile Val Gly Leu Arg Gly Glu Leu Asn
65                  70                  75                  80

Ser Leu Ala Ala Ser Val Gln Thr Ile Gln Ser Ser Leu Arg Ser Leu
            85                  90                  95

Thr Asp Ser Val Ser Asp Leu Ser Gly Gln Val Thr Thr Asn Ala Ser
        100                 105                 110
```

```
Ser Ile Thr Asn Val Lys Gly Met Leu Asp Gly Leu Thr Val Asp Val
        115                 120                 125

Ala Asn Leu Lys Arg Asp Ala Ser Asn Gln Gly Leu Lys Ile Thr Asp
        130                 135                 140

Leu Glu Gln Arg Val Ala Gly Leu Glu Ser Gly Ser Gly Ser Ile Pro
145                 150                 155                 160

Thr Phe Ala Ala Pro Leu Lys Leu Asp Ser Gly Ile Val Ser Leu Asp
                165                 170                 175

Leu Asp Pro Tyr Phe Cys Ser Val Asp His Asn Leu Thr Ser Tyr Ser
            180                 185                 190

Ala Ser Ala Ser Leu Met Asn Phe Gln Trp Leu Val Arg Gly Glu Gly
        195                 200                 205

Gly Ser Ser Asp Ser Phe Asp Met Asn Val Thr Ala His Ser His Gly
        210                 215                 220

Gln Arg Thr Asp Tyr Met Met Ser Thr Thr Gln Ser Leu Thr Val Thr
225                 230                 235                 240

Gly Asn Ser Val Thr Leu Val Phe Asp Leu Asn Ala Leu Ile Ser Pro
                245                 250                 255

Pro Ser Asp Tyr Ser Arg Leu Ile Pro Cys His Gly Phe Gln Gln Ala
            260                 265                 270

Thr Phe Pro Val Asp Leu Ser Phe Lys Arg Asp Asp Val Thr His Ser
        275                 280                 285

Tyr Gln Val Tyr Gly Ser Tyr Thr Thr Pro Arg Val Phe Lys Ile Thr
290                 295                 300

Phe Ser Pro Gly Asn Pro Val Pro Ala Val Ile Arg Phe Ile Thr Gly
305                 310                 315                 320

Asp

<210> SEQ ID NO 23
<211> LENGTH: 978
<212> TYPE: DNA
<213> ORGANISM: Avian orthoreovirus
<220> FEATURE:
<221> NAME/KEY: CDS
<222> LOCATION: (1)..(978)
<220> FEATURE:
<221> NAME/KEY: misc_feature
<222> LOCATION: (161)..(161)
<223> OTHER INFORMATION: k = g or t

<400> SEQUENCE: 23 atg gcc gga tta act ccc tca cag cga aga gaa gtc gtg gga ttg ata      48
Met Ala Gly Leu Thr Pro Ser Gln Arg Arg Glu Val Val Gly Leu Ile
1               5                   10                  15 ctc tcc ttg act tcg agc gcg aat aca aat tgt gga gat ttg acg ccc      96
Leu Ser Leu Thr Ser Ser Ala Asn Thr Asn Cys Gly Asp Leu Thr Pro
            20                  25                  30 gtg tat gat cgt ctg ctc agt ctg gag tcc gct gtt gca tca ctg aat     144
Val Tyr Asp Arg Leu Leu Ser Leu Glu Ser Ala Val Ala Ser Leu Asn
        35                  40                  45 ggc tct gtt agc ggc tcg tct cag aag gtg tta gat ttg gag tca ggt     192
Gly Ser Val Ser Gly Ser Ser Gln Lys Val Leu Asp Leu Glu Ser Gly
50                  55                  60 tta caa gac gtc gct tca tct tta ggc cag act aat tca acg ttg act     240
Leu Gln Asp Val Ala Ser Ser Leu Gly Gln Thr Asn Ser Thr Leu Thr
65                  70                  75                  80 gag tta tcg aaa gga ctg cgt cag ctg agc agt tcc gtt gac agc ctc     288
Glu Leu Ser Lys Gly Leu Arg Gln Leu Ser Ser Val Asp Ser Leu
                85                  90                  95
```

```
gtc tcg tct gtt tca gat cta tcg acc gct gtg tcc ggg cat caa gac      336
Val Ser Ser Val Ser Asp Leu Ser Thr Ala Val Ser Gly His Gln Asp
        100                 105                 110 gcc ata gtt act att caa acg tcc gtc cac gct aac tca act gat atc      384
Ala Ile Val Thr Ile Gln Thr Ser Val His Ala Asn Ser Thr Asp Ile
        115                 120                 125 agt aac ctg aga agc agc gta tct acc att agc ttg aat atc acc gat      432
Ser Asn Leu Arg Ser Ser Val Ser Thr Ile Ser Leu Asn Ile Thr Asp
        130                 135                 140 ctc gag caa cgc gtg gaa aag att gaa tca ggc gca agc tcc agt cta      480
Leu Glu Gln Arg Val Glu Lys Ile Glu Ser Gly Ala Ser Ser Ser Leu
145                 150                 155                 160 cgg ttt acg tcg cct ctg agt ttg tct caa ggc gtg gtg tca ctg att      528
Arg Phe Thr Ser Pro Leu Ser Leu Ser Gln Gly Val Val Ser Leu Ile
                165                 170                 175 atg gat cct tac ttc tgt tca gac aac atg gca cta acc tca tat tct      576
Met Asp Pro Tyr Phe Cys Ser Asp Asn Met Ala Leu Thr Ser Tyr Ser
                180                 185                 190 aca gat gct caa ctg atg cag ttt cag tgg ttg gct aga ggt gag gat      624
Thr Asp Ala Gln Leu Met Gln Phe Gln Trp Leu Ala Arg Gly Glu Asp
        195                 200                 205 ggg tca tca agc tct gtt gat atg ctc gtt aat gct cac tgt cat ggg      672
Gly Ser Ser Ser Ser Val Asp Met Leu Val Asn Ala His Cys His Gly
        210                 215                 220 cgt cgc act gat tat atg atg tcc acc aaa gag agt ttc act gtt acg      720
Arg Arg Thr Asp Tyr Met Met Ser Thr Lys Glu Ser Phe Thr Val Thr
225                 230                 235                 240 ggc aat tct gtg tcc ttg gtt ttc aat ctg gac tat att act aaa ccg      768
Gly Asn Ser Val Ser Leu Val Phe Asn Leu Asp Tyr Ile Thr Lys Pro
                245                 250                 255 ccc tct gac atg tcg cgt tta gta ccc cgc gct gga ttc cgg gct gct      816
Pro Ser Asp Met Ser Arg Leu Val Pro Arg Ala Gly Phe Arg Ala Ala
                260                 265                 270 tct ttt cct gta gac gtc tct ttc acc cgt gac aca aca ccg cat gct      864
Ser Phe Pro Val Asp Val Ser Phe Thr Arg Asp Thr Thr Pro His Ala
        275                 280                 285 tac cag gtg tac ggt gcc ttc tct agt cct cgc atc ttt aag att aca      912
Tyr Gln Val Tyr Gly Ala Phe Ser Ser Pro Arg Ile Phe Lys Ile Thr
        290                 295                 300 ttc ctt aca ggt ggc act ggg act gca aat ctc cgt ttc ttg acc gtg      960
Phe Leu Thr Gly Gly Thr Gly Thr Ala Asn Leu Arg Phe Leu Thr Val
305                 310                 315                 320 cgt acg ggc atc gac acc                                              978
Arg Thr Gly Ile Asp Thr
                325

<210> SEQ ID NO 24
<211> LENGTH: 326
<212> TYPE: PRT
<213> ORGANISM: Avian orthoreovirus

<400> SEQUENCE: 24

Met Ala Gly Leu Thr Pro Ser Gln Arg Arg Glu Val Val Gly Leu Ile
1               5                   10                  15

Leu Ser Leu Thr Ser Ser Ala Asn Thr Asn Cys Gly Asp Leu Thr Pro
            20                  25                  30

Val Tyr Asp Arg Leu Leu Ser Leu Glu Ser Ala Val Ala Ser Leu Asn
        35                  40                  45

Gly Ser Val Ser Gly Ser Ser Gln Lys Val Leu Asp Leu Glu Ser Gly
    50                  55                  60
```

```
Leu Gln Asp Val Ala Ser Ser Leu Gly Gln Thr Asn Ser Thr Leu Thr
 65                  70                  75                  80

Glu Leu Ser Lys Gly Leu Arg Gln Leu Ser Ser Val Asp Ser Leu
             85                   90                  95

Val Ser Ser Val Ser Asp Leu Ser Thr Ala Val Ser Gly His Gln Asp
            100                 105                 110

Ala Ile Val Thr Ile Gln Thr Ser Val His Ala Asn Ser Thr Asp Ile
        115                 120                 125

Ser Asn Leu Arg Ser Ser Val Ser Thr Ile Ser Leu Asn Ile Thr Asp
130                 135                 140

Leu Glu Gln Arg Val Glu Lys Ile Glu Ser Gly Ala Ser Ser Ser Leu
145                 150                 155                 160

Arg Phe Thr Ser Pro Leu Ser Leu Ser Gln Gly Val Val Ser Leu Ile
                165                 170                 175

Met Asp Pro Tyr Phe Cys Ser Asp Asn Met Ala Leu Thr Ser Tyr Ser
            180                 185                 190

Thr Asp Ala Gln Leu Met Gln Phe Gln Trp Leu Ala Arg Gly Glu Asp
        195                 200                 205

Gly Ser Ser Ser Val Asp Met Leu Val Asn Ala His Cys His Gly
210                 215                 220

Arg Arg Thr Asp Tyr Met Met Ser Thr Lys Glu Ser Phe Thr Val Thr
225                 230                 235                 240

Gly Asn Ser Val Ser Leu Val Phe Asn Leu Asp Tyr Ile Thr Lys Pro
                245                 250                 255

Pro Ser Asp Met Ser Arg Leu Val Pro Arg Ala Gly Phe Arg Ala Ala
            260                 265                 270

Ser Phe Pro Val Asp Val Ser Phe Thr Arg Asp Thr Thr Pro His Ala
        275                 280                 285

Tyr Gln Val Tyr Gly Ala Phe Ser Ser Pro Arg Ile Phe Lys Ile Thr
    290                 295                 300

Phe Leu Thr Gly Gly Thr Gly Thr Ala Asn Leu Arg Phe Leu Thr Val
305                 310                 315                 320

Arg Thr Gly Ile Asp Thr
                325

<210> SEQ ID NO 25
<211> LENGTH: 951
<212> TYPE: DNA
<213> ORGANISM: Avian orthoreovirus
<220> FEATURE:
<221> NAME/KEY: CDS
<222> LOCATION: (1)..(951)

<400> SEQUENCE: 25 atg gac gga tta act ccc tca cag cga aga gaa gtc gtg gga ttg ata      48
Met Asp Gly Leu Thr Pro Ser Gln Arg Arg Glu Val Val Gly Leu Ile
1               5                   10                  15 ctc tcc ttg act tcg agc gtg aat aca aac tgt gga gat ttg acg cct      96
Leu Ser Leu Thr Ser Ser Val Asn Thr Asn Cys Gly Asp Leu Thr Pro
            20                  25                  30 gta tac gac cgt ctg ctt agt ctg gag tcc gcc gtt gcg tcg ctg aac     144
Val Tyr Asp Arg Leu Leu Ser Leu Glu Ser Ala Val Ala Ser Leu Asn
        35                  40                  45 aac tct gtt aat gac ttg ttg cag aag gta tca gat ttt gaa tct gac     192
Asn Ser Val Asn Asp Leu Leu Gln Lys Val Ser Asp Phe Glu Ser Asp
50                  55                  60 ttg caa gac gcc acc tca tct cta ggc caa gcc aat ttg atg cta acc     240
```

```
Leu Gln Asp Ala Thr Ser Ser Leu Gly Gln Ala Asn Leu Met Leu Thr
 65                  70                  75                  80 aag tta tct gag gac ttg cgt cag ttg agc agc tct gtt gac aac ctc      288
Lys Leu Ser Glu Asp Leu Arg Gln Leu Ser Ser Ser Val Asp Asn Leu
                 85                  90                  95 gtc acg tcc gtt tct gat cta tcg acc act gta tcc ggg cat cag gac      336
Val Thr Ser Val Ser Asp Leu Ser Thr Thr Val Ser Gly His Gln Asp
            100                 105                 110 gca ata gcc gct ata caa act tcc gtt cat gcc aat aca acc gat att      384
Ala Ile Ala Ala Ile Gln Thr Ser Val His Ala Asn Thr Thr Asp Ile
        115                 120                 125 agt aac tta aaa agc aac gta tct act att ggc ttg aat atc aca gat      432
Ser Asn Leu Lys Ser Asn Val Ser Thr Ile Gly Leu Asn Ile Thr Asp
    130                 135                 140 ctc gcg caa cgt gtg gca aac att gaa tca agc tcg ggc tct agt tta      480
Leu Ala Gln Arg Val Ala Asn Ile Glu Ser Ser Ser Gly Ser Ser Leu
145                 150                 155                 160 aga ttt gtg tca cct ctg agc ttg tcc caa ggt gta gtg tcc ttg atc      528
Arg Phe Val Ser Pro Leu Ser Leu Ser Gln Gly Val Val Ser Leu Ile
                165                 170                 175 atg gat ccc tac ttc tgt tcg gac aat aag gca tta acc tcc tat tcc      576
Met Asp Pro Tyr Phe Cys Ser Asp Asn Lys Ala Leu Thr Ser Tyr Ser
            180                 185                 190 acg gac gct cag ctg atg cag ttc cag tgg ctg gct aga ggt gag gat      624
Thr Asp Ala Gln Leu Met Gln Phe Gln Trp Leu Ala Arg Gly Glu Asp
        195                 200                 205 ggg tca tcg agc tct gtt gat atg ctt gtt aac gca cac tgt cat ggg      672
Gly Ser Ser Ser Ser Val Asp Met Leu Val Asn Ala His Cys His Gly
    210                 215                 220 cgt cgc act gat tat atg atg tcc act aca gag agt ttt act gtc acg      720
Arg Arg Thr Asp Tyr Met Met Ser Thr Thr Glu Ser Phe Thr Val Thr
225                 230                 235                 240 ggc aat tct gta tca ttg gtc ttc aac ctg gat tat atc acc aaa ccg      768
Gly Asn Ser Val Ser Leu Val Phe Asn Leu Asp Tyr Ile Thr Lys Pro
                245                 250                 255 ccc tct gac atg tcg cgg cta gta cca cgt gct ggt ttc cag gct gct      816
Pro Ser Asp Met Ser Arg Leu Val Pro Arg Ala Gly Phe Gln Ala Ala
            260                 265                 270 tct ttc cct gtg gac gtc tcc ttc act cgt gac aca aca ccg cac gct      864
Ser Phe Pro Val Asp Val Ser Phe Thr Arg Asp Thr Thr Pro His Ala
        275                 280                 285 tac cag gtg tac ggc gct ttc tct agc cct cgc att ttt aag atc acg      912
Tyr Gln Val Tyr Gly Ala Phe Ser Ser Pro Arg Ile Phe Lys Ile Thr
    290                 295                 300 ttc ctc aca ggc ggt act gga act gca aat ctc cgt ttc                  951
Phe Leu Thr Gly Gly Thr Gly Thr Ala Asn Leu Arg Phe
305                 310                 315

<210> SEQ ID NO 26
<211> LENGTH: 317
<212> TYPE: PRT
<213> ORGANISM: Avian orthoreovirus

<400> SEQUENCE: 26

Met Asp Gly Leu Thr Pro Ser Gln Arg Arg Glu Val Val Gly Leu Ile
1               5                   10                  15

Leu Ser Leu Thr Ser Ser Val Asn Thr Asn Cys Gly Asp Leu Thr Pro
            20                  25                  30

Val Tyr Asp Arg Leu Leu Ser Leu Glu Ser Ala Val Ala Ser Leu Asn
        35                  40                  45
```

```
Asn Ser Val Asn Asp Leu Leu Gln Lys Val Ser Asp Phe Glu Ser Asp
         50                  55                  60

Leu Gln Asp Ala Thr Ser Ser Leu Gly Gln Ala Asn Leu Met Leu Thr
 65                  70                  75                  80

Lys Leu Ser Glu Asp Leu Arg Gln Leu Ser Ser Val Asp Asn Leu
                 85                  90                  95

Val Thr Ser Val Ser Asp Leu Ser Thr Thr Val Ser Gly His Gln Asp
                100                 105                 110

Ala Ile Ala Ala Ile Gln Thr Ser Val His Ala Asn Thr Thr Asp Ile
            115                 120                 125

Ser Asn Leu Lys Ser Asn Val Ser Thr Ile Gly Leu Asn Ile Thr Asp
        130                 135                 140

Leu Ala Gln Arg Val Ala Asn Ile Glu Ser Ser Gly Ser Ser Leu
145                 150                 155                 160

Arg Phe Val Ser Pro Leu Ser Leu Ser Gln Gly Val Val Ser Leu Ile
                165                 170                 175

Met Asp Pro Tyr Phe Cys Ser Asp Asn Lys Ala Leu Thr Ser Tyr Ser
            180                 185                 190

Thr Asp Ala Gln Leu Met Gln Phe Gln Trp Leu Ala Arg Gly Glu Asp
        195                 200                 205

Gly Ser Ser Ser Val Asp Met Leu Val Asn Ala His Cys His Gly
                210                 215                 220

Arg Arg Thr Asp Tyr Met Met Ser Thr Thr Glu Ser Phe Thr Val Thr
225                 230                 235                 240

Gly Asn Ser Val Ser Leu Val Phe Asn Leu Asp Tyr Ile Thr Lys Pro
                245                 250                 255

Pro Ser Asp Met Ser Arg Leu Val Pro Arg Ala Gly Phe Gln Ala Ala
            260                 265                 270

Ser Phe Pro Val Asp Val Ser Phe Thr Arg Asp Thr Thr Pro His Ala
        275                 280                 285

Tyr Gln Val Tyr Gly Ala Phe Ser Ser Pro Arg Ile Phe Lys Ile Thr
    290                 295                 300

Phe Leu Thr Gly Gly Thr Gly Thr Ala Asn Leu Arg Phe
305                 310                 315

<210> SEQ ID NO 27
<211> LENGTH: 966
<212> TYPE: DNA
<213> ORGANISM: Avian orthoreovirus
<220> FEATURE:
<221> NAME/KEY: CDS
<222> LOCATION: (1)..(966)

<400> SEQUENCE: 27 atg gaa ggt tta agt cag tta cag cga aga gaa gtc gtg ggg ctg ata        48
Met Glu Gly Leu Ser Gln Leu Gln Arg Arg Glu Val Val Gly Leu Ile
1               5                   10                  15 ctc tcg ttg act tcg aac gtg act ata agt cct ggc gat tta acg gaa        96
Leu Ser Leu Thr Ser Asn Val Thr Ile Ser Pro Gly Asp Leu Thr Glu
            20                  25                  30 ctg cgt gaa cgc gtc tca gcg tta gaa tct gct act gcg tcg ttg aat       144
Leu Arg Glu Arg Val Ser Ala Leu Glu Ser Ala Thr Ala Ser Leu Asn
        35                  40                  45 gag act gta aag ggc gtg cta ggt cag ctg gtg gat ttg gcg cag aag       192
Glu Thr Val Lys Gly Val Leu Gly Gln Leu Val Asp Leu Ala Gln Lys
    50                  55                  60 ttg agc aac gcg gca gat gct gtg gtt gag ctc cga gga gat ttg aat       240
Leu Ser Asn Ala Ala Asp Ala Val Val Glu Leu Arg Gly Asp Leu Asn
```

```
                    65                   70                   75                   80
tca tta acc gtt agc gtc caa act atc caa tcc tct ttg gga tca ctt            288
Ser Leu Thr Val Ser Val Gln Thr Ile Gln Ser Ser Leu Gly Ser Leu
                    85                   90                   95 aca gaa agc atg tcg gat ctt tcc ggc cag gtg act act aat gct tcg            336
Thr Glu Ser Met Ser Asp Leu Ser Gly Gln Val Thr Thr Asn Ala Ser
                100                  105                  110 tcg atc acg aat ttg agg agt gtg gtg gat ggt ctc aca gtc gac gtg            384
Ser Ile Thr Asn Leu Arg Ser Val Val Asp Gly Leu Thr Val Asp Val
                115                  120                  125 gct aat ctt aag cgc gac atg tca aac cag ggt ctt aaa gtc act ggt            432
Ala Asn Leu Lys Arg Asp Met Ser Asn Gln Gly Leu Lys Val Thr Gly
            130                  135                  140 ctc gag cag cgt gta gct gat ttg gag tct ggc gct gga tct ctt ccc            480
Leu Glu Gln Arg Val Ala Asp Leu Glu Ser Gly Ala Gly Ser Leu Pro
145                 150                  155                  160 aca ttt gct gct ccc ctt aaa tta gat agc ggg gtt gta tca ctc gac            528
Thr Phe Ala Ala Pro Leu Lys Leu Asp Ser Gly Val Val Ser Leu Asp
                165                  170                  175 ctg gat cct tac ttt tgt tct gtg gac cat aat ctt acg tcg tat tcc            576
Leu Asp Pro Tyr Phe Cys Ser Val Asp His Asn Leu Thr Ser Tyr Ser
                180                  185                  190 gca agt gca tcg tta atg aat ttt cag tgg ctc gtt cga ggt gag ggc            624
Ala Ser Ala Ser Leu Met Asn Phe Gln Trp Leu Val Arg Gly Glu Gly
                195                  200                  205 gga tcg tct gac tct ttc gat atg aat gtg aca gct cat agc cat ggc            672
Gly Ser Ser Asp Ser Phe Asp Met Asn Val Thr Ala His Ser His Gly
            210                  215                  220 cag agg aca gac tat atg atg tct act act caa tca ttg act gtt act            720
Gln Arg Thr Asp Tyr Met Met Ser Thr Thr Gln Ser Leu Thr Val Thr
225                 230                  235                  240 gga aat tca gtc acc cta gtc ttt gat ctt aac gcc ctt att tct cca            768
Gly Asn Ser Val Thr Leu Val Phe Asp Leu Asn Ala Leu Ile Ser Pro
                245                  250                  255 ccc tct gat tac tct cgc ttg ata cca tgt cat ggc ttc caa caa gcg            816
Pro Ser Asp Tyr Ser Arg Leu Ile Pro Cys His Gly Phe Gln Gln Ala
                260                  265                  270 acg ttc cca gtg gac ctt tcg ttt aag cga gat gac gtc ata cac tca            864
Thr Phe Pro Val Asp Leu Ser Phe Lys Arg Asp Asp Val Ile His Ser
                275                  280                  285 tat cag gtg tat ggt tcg tac aca act ccc cgc gtt ttc agg ata aca            912
Tyr Gln Val Tyr Gly Ser Tyr Thr Thr Pro Arg Val Phe Arg Ile Thr
            290                  295                  300 ttc tct ccc ggc aat cca gtg ccc gcg gtc ata cgc ttc ata acc ggc            960
Phe Ser Pro Gly Asn Pro Val Pro Ala Val Ile Arg Phe Ile Thr Gly
305                 310                  315                  320 gac gag                                                                    966
Asp Glu <210> SEQ ID NO 28
<211> LENGTH: 322
<212> TYPE: PRT
<213> ORGANISM: Avian orthoreovirus

<400> SEQUENCE: 28

Met Glu Gly Leu Ser Gln Leu Gln Arg Arg Glu Val Val Gly Leu Ile
1               5                   10                  15

Leu Ser Leu Thr Ser Asn Val Thr Ile Ser Pro Gly Asp Leu Thr Glu
            20                  25                  30

Leu Arg Glu Arg Val Ser Ala Leu Glu Ser Ala Thr Ala Ser Leu Asn
```

```
                    35                  40                  45
Glu Thr Val Lys Gly Val Leu Gly Gln Leu Val Asp Leu Ala Gln Lys
50                  55                  60

Leu Ser Asn Ala Ala Asp Ala Val Val Glu Leu Arg Gly Asp Leu Asn
65                  70                  75                  80

Ser Leu Thr Val Ser Val Gln Thr Ile Gln Ser Ser Leu Gly Ser Leu
                85                  90                  95

Thr Glu Ser Met Ser Asp Leu Ser Gly Gln Val Thr Asn Ala Ser
            100                 105                 110

Ser Ile Thr Asn Leu Arg Ser Val Val Asp Gly Leu Thr Val Asp Val
        115                 120                 125

Ala Asn Leu Lys Arg Asp Met Ser Asn Gln Gly Leu Lys Val Thr Gly
130                 135                 140

Leu Glu Gln Arg Val Ala Asp Leu Glu Ser Gly Ala Gly Ser Leu Pro
145                 150                 155                 160

Thr Phe Ala Ala Pro Leu Lys Leu Asp Ser Gly Val Val Ser Leu Asp
                165                 170                 175

Leu Asp Pro Tyr Phe Cys Ser Val Asp His Asn Leu Thr Ser Tyr Ser
            180                 185                 190

Ala Ser Ala Ser Leu Met Asn Phe Gln Trp Leu Val Arg Gly Glu Gly
        195                 200                 205

Gly Ser Ser Asp Ser Phe Asp Met Asn Val Thr Ala His Ser His Gly
210                 215                 220

Gln Arg Thr Asp Tyr Met Met Ser Thr Thr Gln Ser Leu Thr Val Thr
225                 230                 235                 240

Gly Asn Ser Val Thr Leu Val Phe Asp Leu Asn Ala Leu Ile Ser Pro
                245                 250                 255

Pro Ser Asp Tyr Ser Arg Leu Ile Pro Cys His Gly Phe Gln Gln Ala
            260                 265                 270

Thr Phe Pro Val Asp Leu Ser Phe Lys Arg Asp Val Ile His Ser
        275                 280                 285

Tyr Gln Val Tyr Gly Ser Tyr Thr Thr Pro Arg Val Phe Arg Ile Thr
290                 295                 300

Phe Ser Pro Gly Asn Pro Val Pro Ala Val Ile Arg Phe Ile Thr Gly
305                 310                 315                 320

Asp Glu

<210> SEQ ID NO 29
<211> LENGTH: 957
<212> TYPE: DNA
<213> ORGANISM: Avian orthoreovirus
<220> FEATURE:
<221> NAME/KEY: CDS
<222> LOCATION: (1)..(957)

<400> SEQUENCE: 29 atg gaa ggc tta act cag tca cag cga aga gag gtc gtg ggg ctg ata    48
Met Glu Gly Leu Thr Gln Ser Gln Arg Arg Glu Val Val Gly Leu Ile
1               5                   10                  15 ctc tca ttg act tcg aac gtg act ata aat cct ggc gat ttg atg gaa    96
Leu Ser Leu Thr Ser Asn Val Thr Ile Asn Pro Gly Asp Leu Met Glu
            20                  25                  30 ctg cgt gag cgc gtc tca gcg tta gaa tcg gtc act gcg tcg ttg aat   144
Leu Arg Glu Arg Val Ser Ala Leu Glu Ser Val Thr Ala Ser Leu Asn
        35                  40                  45 ggg act ata aaa ggc gtg tta gac cag ctg gtg gat ttg gca cag aag   192
Gly Thr Ile Lys Gly Val Leu Asp Gln Leu Val Asp Leu Ala Gln Lys
```

```
tta ggt aat gcg gcg ggt gct gta gtt gac cta cga ggc gag ctg aac    240
Leu Gly Asn Ala Ala Gly Ala Val Val Asp Leu Arg Gly Glu Leu Asn
65              70                  75                  80 tca tta act gcc agc gtt caa act gtc caa tcc tct ttg gaa tca ctc    288
Ser Leu Thr Ala Ser Val Gln Thr Val Gln Ser Ser Leu Glu Ser Leu
                85                  90                  95 acg gac agt atg tcg gat ctt tct ggc caa gtg act act aac acc tcg    336
Thr Asp Ser Met Ser Asp Leu Ser Gly Gln Val Thr Thr Asn Thr Ser
        100                 105                 110 tcg ctc acg aat ctg gag agt acg gtg gct ggt ctt aca gtc gat gta    384
Ser Leu Thr Asn Leu Glu Ser Thr Val Ala Gly Leu Thr Val Asp Val
    115                 120                 125 act aat ctt aaa cgt gac gta tcg agt cag ggt ctt caa att acg agt    432
Thr Asn Leu Lys Arg Asp Val Ser Ser Gln Gly Leu Gln Ile Thr Ser
130                 135                 140 ctc gag cag cgt gta act agt ttg gaa tct ggc gct gga tct att ccc    480
Leu Glu Gln Arg Val Thr Ser Leu Glu Ser Gly Ala Gly Ser Ile Pro
145                 150                 155                 160 acg ttt gct gct ccc ctt aaa tta gat agc ggg att gta tca ctc gac    528
Thr Phe Ala Ala Pro Leu Lys Leu Asp Ser Gly Ile Val Ser Leu Asp
                165                 170                 175 ttg gat cct tac ttt tgt tct gta gac cat aac ctc acg tcg tat tcc    576
Leu Asp Pro Tyr Phe Cys Ser Val Asp His Asn Leu Thr Ser Tyr Ser
        180                 185                 190 gca agc gct ctg cta atg aat ttt cag tgg ctt gtt cga ggt gag gga    624
Ala Ser Ala Leu Leu Met Asn Phe Gln Trp Leu Val Arg Gly Glu Gly
    195                 200                 205 gga tcg tct gat tca ttc gat atg aat gtg aca gct cat agc cat ggt    672
Gly Ser Ser Asp Ser Phe Asp Met Asn Val Thr Ala His Ser His Gly
210                 215                 220 cag agg aca gac ttt atg atg tct act acc cag tcg tta act gtt act    720
Gln Arg Thr Asp Phe Met Met Ser Thr Thr Gln Ser Leu Thr Val Thr
225                 230                 235                 240 gga aat tct gtc act cta gtc ttt gat ctt aac gcg ctt att tct cca    768
Gly Asn Ser Val Thr Leu Val Phe Asp Leu Asn Ala Leu Ile Ser Pro
                245                 250                 255 ccc cct gac tac tct cgc ttg ata ccc tgc cat ggt ttt caa caa gcg    816
Pro Pro Asp Tyr Ser Arg Leu Ile Pro Cys His Gly Phe Gln Gln Ala
        260                 265                 270 acg ttc cca gtg gac ctt tcg ttc aag cga gac gac gtc acg cac tca    864
Thr Phe Pro Val Asp Leu Ser Phe Lys Arg Asp Asp Val Thr His Ser
    275                 280                 285 tat cag gtg tat ggt tcg tac acg act cct cgc att ttc aag ata acc    912
Tyr Gln Val Tyr Gly Ser Tyr Thr Thr Pro Arg Ile Phe Lys Ile Thr
290                 295                 300 ttc tct cct ggc aat acc agt gcc tgc ggt cat acg ttt ata agc        957
Phe Ser Pro Gly Asn Thr Ser Ala Cys Gly His Thr Phe Ile Ser
305                 310                 315
```

<210> SEQ ID NO 30
<211> LENGTH: 319
<212> TYPE: PRT
<213> ORGANISM: Avian orthoreovirus

<400> SEQUENCE: 30

```
Met Glu Gly Leu Thr Gln Ser Gln Arg Arg Glu Val Val Gly Leu Ile
1               5                   10                  15

Leu Ser Leu Thr Ser Asn Val Thr Ile Asn Pro Gly Asp Leu Met Glu
            20                  25                  30
```

```
Leu Arg Glu Arg Val Ser Ala Leu Glu Ser Val Thr Ala Ser Leu Asn
            35                  40                  45
Gly Thr Ile Lys Gly Val Leu Asp Gln Leu Val Asp Leu Ala Gln Lys
 50                  55                  60
Leu Gly Asn Ala Ala Gly Ala Val Val Asp Leu Arg Gly Glu Leu Asn
 65                  70                  75                  80
Ser Leu Thr Ala Ser Val Gln Thr Val Gln Ser Ser Leu Glu Ser Leu
                85                  90                  95
Thr Asp Ser Met Ser Asp Leu Ser Gly Gln Val Thr Thr Asn Thr Ser
            100                 105                 110
Ser Leu Thr Asn Leu Glu Ser Thr Val Ala Gly Leu Thr Val Asp Val
            115                 120                 125
Thr Asn Leu Lys Arg Asp Val Ser Ser Gln Gly Leu Gln Ile Thr Ser
130                 135                 140
Leu Glu Gln Arg Val Thr Ser Leu Glu Ser Gly Ala Gly Ser Ile Pro
145                 150                 155                 160
Thr Phe Ala Ala Pro Leu Lys Leu Asp Ser Gly Ile Val Ser Leu Asp
                165                 170                 175
Leu Asp Pro Tyr Phe Cys Ser Val Asp His Asn Leu Thr Ser Tyr Ser
            180                 185                 190
Ala Ser Ala Leu Leu Met Asn Phe Gln Trp Leu Val Arg Gly Glu Gly
            195                 200                 205
Gly Ser Ser Asp Ser Phe Asp Met Asn Val Thr Ala His Ser His Gly
            210                 215                 220
Gln Arg Thr Asp Phe Met Met Ser Thr Thr Gln Ser Leu Thr Val Thr
225                 230                 235                 240
Gly Asn Ser Val Thr Leu Val Phe Asp Leu Asn Ala Leu Ile Ser Pro
                245                 250                 255
Pro Pro Asp Tyr Ser Arg Leu Ile Pro Cys His Gly Phe Gln Gln Ala
            260                 265                 270
Thr Phe Pro Val Asp Leu Ser Phe Lys Arg Asp Asp Val Thr His Ser
            275                 280                 285
Tyr Gln Val Tyr Gly Ser Tyr Thr Thr Pro Arg Ile Phe Lys Ile Thr
            290                 295                 300
Phe Ser Pro Gly Asn Thr Ser Ala Cys Gly His Thr Phe Ile Ser
305                 310                 315
```

<210> SEQ ID NO 31
<211> LENGTH: 20
<212> TYPE: DNA
<213> ORGANISM: Artificial Sequence
<220> FEATURE:
<223> OTHER INFORMATION: Synthetic Primer

<400> SEQUENCE: 31
agtatttgtg agtacgattg                                         20

<210> SEQ ID NO 32
<211> LENGTH: 17
<212> TYPE: DNA
<213> ORGANISM: Artificial Sequence
<220> FEATURE:
<223> OTHER INFORMATION: Synthetic Primer

<400> SEQUENCE: 32
ggcgccacac cttaggt                                            17

The invention claimed is:

1. An isolated avian reovirus comprising an S1 protein, wherein the S1 protein comprises an amino acid sequence selected from the group consisting of SEQ ID NOS: 2, 4, 6, 8, 10, 12, 14, 16, 18, 20, 22, 24, 26, 28, and 30.

2. The isolated avian reovirus of claim 1, wherein the isolated reovirus is designated strain 40973 and has ATCC accession number PTA-7174, or a progeny thereof.

3. A composition comprising the isolated avian reovirus of claim 1.

4. The composition of claim 3, further comprising a pharmaceutically acceptable carrier, adjuvant, or diluent.

5. The composition of claim 3, comprising at least $10^2$ titration units of the reovirus.

* * * * *